United States Patent
Hegde et al.

(12) 
(10) Patent No.: US 6,573,286 B1
(45) Date of Patent: Jun. 3, 2003

(54) 2-(2,6-DISUBSTITUTED PHENYL)-4-ARYL-5-ALKYL-1,3-OXAZOLINE COMPOUNDS

(75) Inventors: Vidyadhar Babu Hegde, Carmel, IN (US); Maurice Chee Hoong Yap, Zionsville, IN (US); Scott Jerome Bis, Midland, MI (US); Timothy Patrick Martin, Indianapolis, IN (US); Denise Marie Perreault, Indianapolis, IN (US); Katherine Anne Guenthenspberger, Daleville, IN (US); Laura Lee Karr, Lebanon, IN (US); Joe Raymond Schoonover, Brownsburg, IN (US); Leonard Paul Dintenfass, Indianapolis, IN (US); James Michael Gifford, Lebanon, IN (US); James Edwin Dripps, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/177,443

(22) Filed: Jun. 21, 2002

(51) Int. Cl.[7] .................. C07D 263/10; A01N 43/76
(52) U.S. Cl. .................. 514/374; 546/271.4; 548/237
(58) Field of Search .................. 548/237; 546/271.4; 514/374

(56) References Cited

FOREIGN PATENT DOCUMENTS

| CH | WO 00/58291 | * 10/2000 |
|---|---|---|
| EP | 0345775 | 6/1989 |
| EP | 0432661 A2 | 6/1991 |
| EP | 0553623 A1 | 8/1993 |
| JP | 04089484 | 3/1992 |
| JP | 06145169 | 5/1994 |
| WO | WO 93/24470 | 12/1993 |
| WO | WO 96/22283 | 7/1996 |
| WO | WO 98/47881 | 10/1998 |
| WO | WO 99/01443 | 1/1999 |
| WO | WO 99/23081 | 5/1999 |
| WO | WO 99/65901 | 12/1999 |
| WO | WO 00/24720 | 5/2000 |
| WO | WO 00/24735 | 5/2000 |
| WO | WO 01/98296 | 12/2001 |

* cited by examiner

*Primary Examiner*—Ceila Chang
*Assistant Examiner*—Kamal Saeed
(74) *Attorney, Agent, or Firm*—Craig E. Mixan

(57) ABSTRACT

Oxazoline compounds having a 2,6-disubstituted-phenyl group in the 2-position, an aryl or heteroaryl group in the 4-position and an alkyl group in the 5-position are effective in controlling aphids, insects and mites.

33 Claims, No Drawings

2-(2,6-DISUBSTITUTED PHENYL)-4-ARYL-5-ALKYL-1,3-OXAZOLINE COMPOUNDS

BACKGROUND OF THE INVENTION

This invention concerns new oxazolines that are useful as insecticides and acaricides. More particularly, the present invention concerns 2-(2,6-disubstituted phenyl)-4-aryl-5-alkyl-1,3-oxazoline compounds and their stereoisomers. This invention also includes new synthetic procedures and intermediates for preparing the compounds, pesticide compositions containing the compounds, and methods of controlling insects and mites using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

2-(Substituted-phenyl)-1,3-oxazolines with insecticidal activity are disclosed in JP 4-89484, EP 0345775-A1, EP 0432661-A2, EP 0553623-A1, WO 99/01443, WO 99/23081 and WO 98/47881. 2-Aryl- and 2-heteroaryl-1,3-oxazolines with acaricidal and insecticidal activity are disclosed in JP 6-145169 and WO 99/65901. Arthropocidal 2-(substituted-phenyl)-1,3-oxazolines are disclosed in WO 93/24470. To the applicants' knowledge, only one oxazoline product, etoxazole, has been developed as a commercial acaricide. It would be highly desirable to discover related compounds of this mode of action that are more potent, more selective or of broader spectrum in their activity and/or that have improved toxicological and environmental properties.

SUMMARY OF THE INVENTION

This invention provides novel 2-(2,6-disubstituted phenyl)-4-aryl-5-alkyl-1,3-oxazoline derivatives especially useful for the control of insects and mites.

More specifically, the invention provides novel insecticidally active compounds of the formula (I)

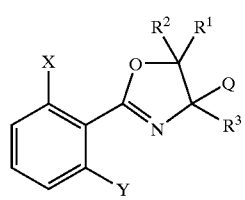

(I)

wherein $R^1$ is $(C_1-C_3)$ alkyl or $(C_1-C_3)$ haloalkyl;

$R^2$ and $R^3$ are independently H, halogen, $(C_1-C_3)$ alkyl, $(C_1-C_3)$ haloalkyl, $(C_1-C_3)$ alkoxy or $(C_1-C_3)$ haloalkoxy;

Q is a group selected from

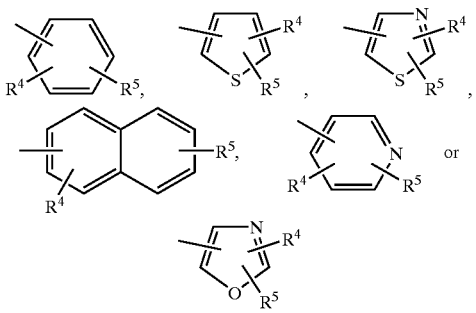

$R^4$ is H, halogen, hydroxy, $(C_1-C_6)$ alkyl, $(C_1-C_6)$ alkoxy, $(C_1-C_6)$ haloalkyl, $(C_1-C_6)$ haloalkoxy, $(C_1-C_6)$ alkoxyalkyl, $(C_1-C_6)$ alkoxyalkoxy, $(C_2-C_6)$ alkenyl, $(C_2-C_6)$ haloalkenyl, CN, $NO_2$, $CO_2R^6$, $CON(R^6)_2$, $S(O)_mR^6$, SCN, $—CH_2OR^6$, $—CH_2SR^6$, $—CH_2NR^6R^6$, $—OCH_2R^6$, $—SCH_2R^6$, $—NR^6CH_2R^6$,

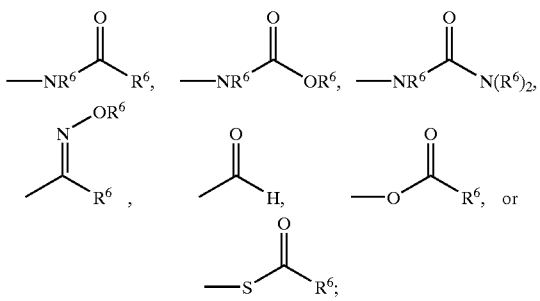

$R^5$ represents

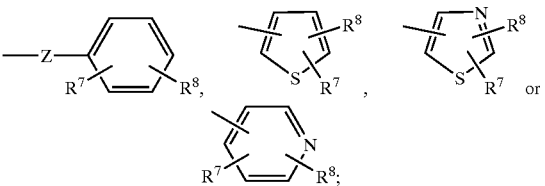

$R^6$ is H, $(C_1-C_6)$ alkyl, $(C_1-C_6)$ haloalkyl, $(C_2-C_6)$ alkenyl, $(C_2-C_6)$ alkynyl, phenyl, or substituted phenyl;

$R^7$ and $R^8$ are independently H, halo, $(C_1-C_6)$ alkyl, $(C_1-C_6)$ haloalkyl, $(C_1-C_6)$ alkoxy or $(C_1-C_6)$ haloalkoxy;

X and Y are independently Cl, F, methyl, halomethyl, methoxy, or halomethoxy;

m is 0, 1, or 2; and

Z is a direct bond, $CH_2$, $CH_2CH_2$, O or S or a phytologically acceptable acid addition salt or N-oxide thereof.

Preferred compounds of formula (I) include the following classes:

(1) Compounds of formula (I) wherein X and Y are both halogen.

(2) Compounds of class (1) wherein X and Y are both F.

(3) Compounds of formula (I) wherein $R^2$ and $R^3$ are H.

(4) Compounds of formula (I) wherein $R^4$ is H, halogen, $(C_1-C_6)$ alkyl, $(C_1-C_6)$ haloalkyl, $(C_1-C_6)$ alkoxy or $(C_1-C_6)$ haloalkoxy.

(5) Compounds of formula (I) wherein Q is

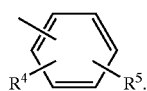

(6) Compounds of class (5) wherein $R^5$ is

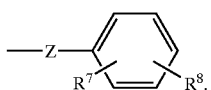

(7) Compounds of formula (I), and particularly compounds of class (6) as defined above, wherein Z is a direct bond.

(8) Compounds of formula (I) wherein $R^1$ is methyl.

It will be appreciated by those skilled in the art that the most preferred compounds are generally those which are comprised of various combinations of the above preferred classes.

Particularly preferred compounds are of formula (Ia)

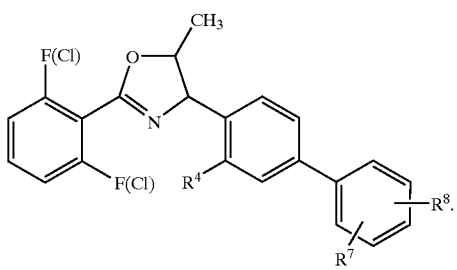

(Ia)

The invention also provides new processes and intermediates for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the terms "alkyl", "alkenyl" and "alkynyl", as well as derivative terms such as "alkoxy" and "alkanoyl", as used herein, include within their scope straight chain, branched chain and cyclic moieties. The terms "alkenyl" and "alkynyl" are intended to include one or more unsaturated bonds.

Unless specifically limited otherwise, the term "halogen", as well as derivative terms such as "halo", as used herein, refer to fluorine, chlorine, bromine, and iodine. Preferred halogens are fluorine and chlorine.

The terms "halomethyl", "haloalkyl", and "haloalkenyl" refer to methyl, alkyl, and alkenyl groups substituted with from one up to the maximum possible number of halo atoms. The terms "halomethoxy" and "haloalkoxy" refer to methoxy and alkoxy groups substituted with from one up to the maximum possible number of halo atoms.

The terms "substituted pyridyl," "substituted isoxazolyl," "substituted thienyl," and "substituted thiazolyl" refer to the ring system substituted with one or more groups independently selected from halo, $(C_1-C_4)$ alkyl, $(C_1-C_4)$ haloalkyl, CN, $NO_2$, phenyl, $(C_1-C_4)$ alkoxy, or $(C_1-C_4)$ haloalkoxy.

The term "substituted phenyl" refers to a phenyl group substituted with one or more groups independently selected from halo, $(C_1-C_{10})$ alkyl, $(C_1-C_7)$ haloalkyl, $(C_1-C_7)$ hydroxyalkyl, $(C_1-C_7)$ alkoxy, $(C_1-C_7)$ haloalkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy.

Unless otherwise indicated, when it is stated that a group may be substituted with one or more substituents selected from an identified class, it is intended that the substituents may be independently selected from the class, provided that the substituents are sterically compatible and the rules of chemical bonding and strain energy are satisfied.

Relative to the oxazoline ring, the compounds of this invention can exist as one or more stereoisomers. The various stereoisomers include geometric isomers, diastereomers and enantiomers. Thus the compounds of the present invention include racemic mixtures, individual stereoisomers and optically active mixtures. For example, for compounds of the formula (Ia)

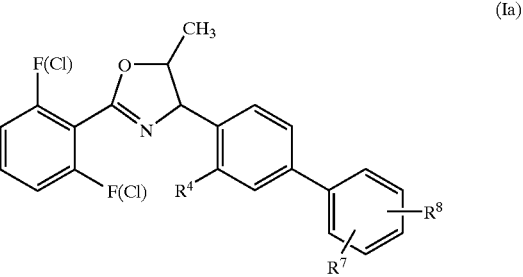

(Ia)

the following stereoisomers are possible:

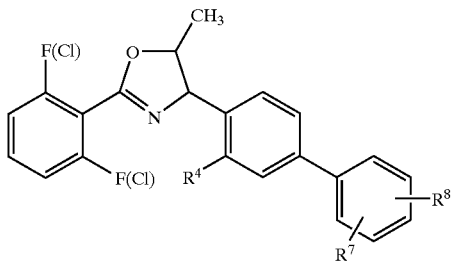

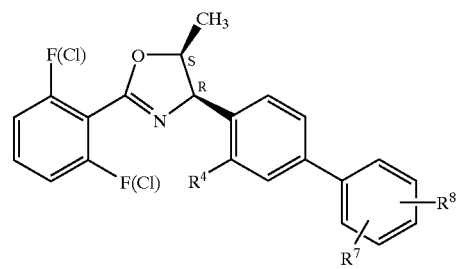

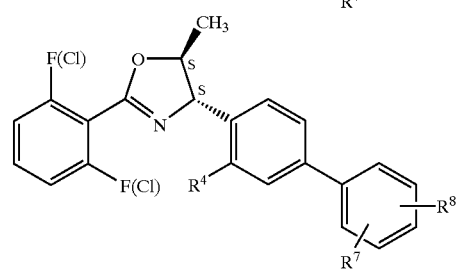

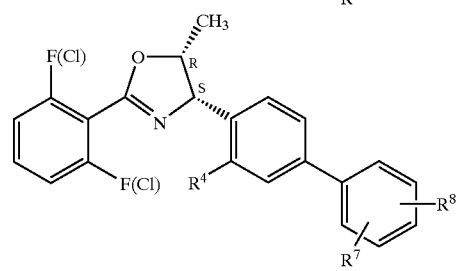

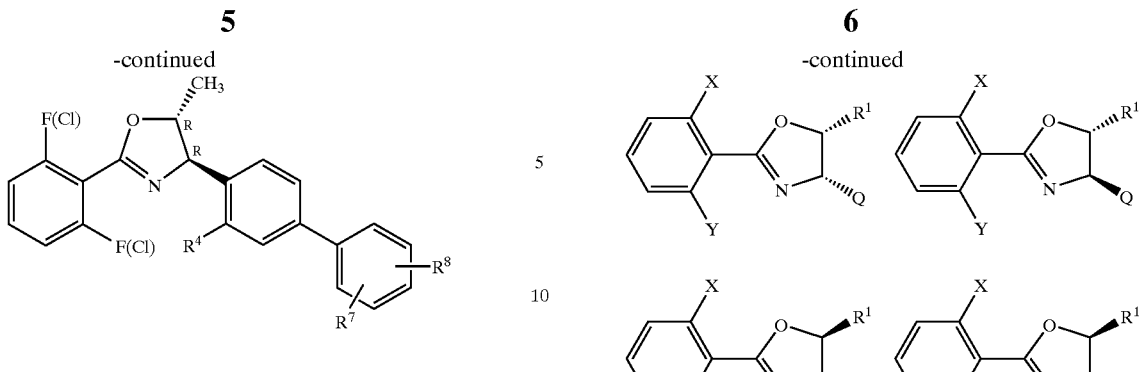

It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

Synthesis

Compounds of formula (I), in particular diastereomers Syn (I) and Anti (I) can be prepared by the method illustrated in Scheme A:

Scheme A

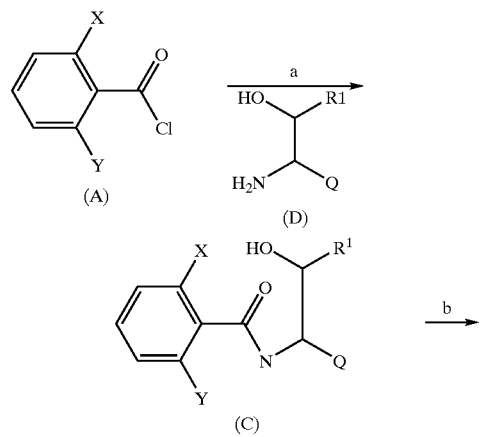

wherein $R^1$, Q, X and Y are as defined in formula (I).

In step a of Scheme A, the compound of formula (A) is reacted with an aminoalcohol (D) to afford a compound of formula (C). 1,2-Dichloroethane is the preferred solvent, however other polar aprotic solvents such as pyridine or THF can also be used.

In step b of Scheme A the N-amidealcohol of formula (C) can be reacted with either (diethylamino)sulfur trifluoride (DAST) or with thionyl chloride to provide the products of formula Syn (I) and Anti (I) which can be separated using chromatographic techniques. The DAST reaction is carried out in dichloromethane or 1,2-dichloroethane at a temperature in the range from −78° C. to ambient temperature. The thionyl chloride reaction is carried out in dichloromethane or 1,2-dichloroethane at a temperature in the range from 0° C. to ambient temperature.

Alternatively, when Q represents

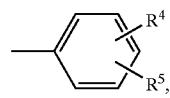

compounds of formula (I), in particular diastereomers Syn (Ic) and Anti (Ic), can be prepared by the method shown in Scheme B:

Scheme B

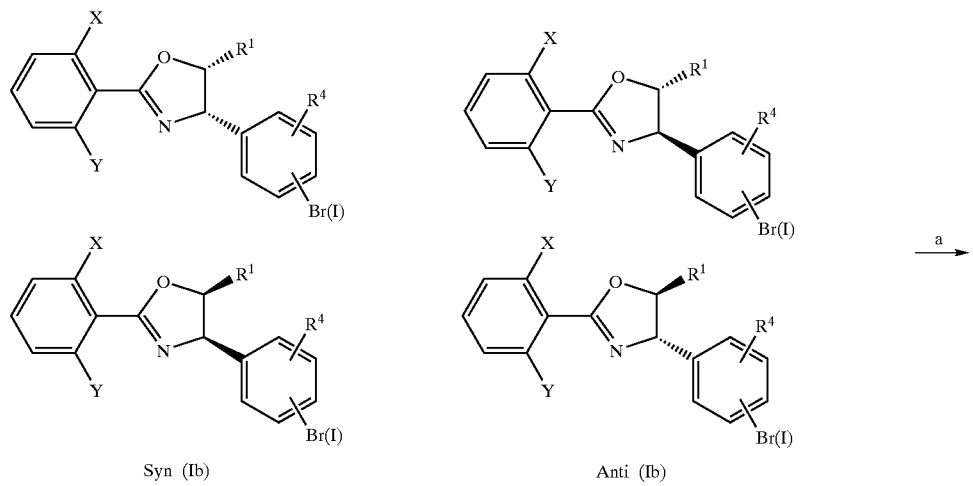

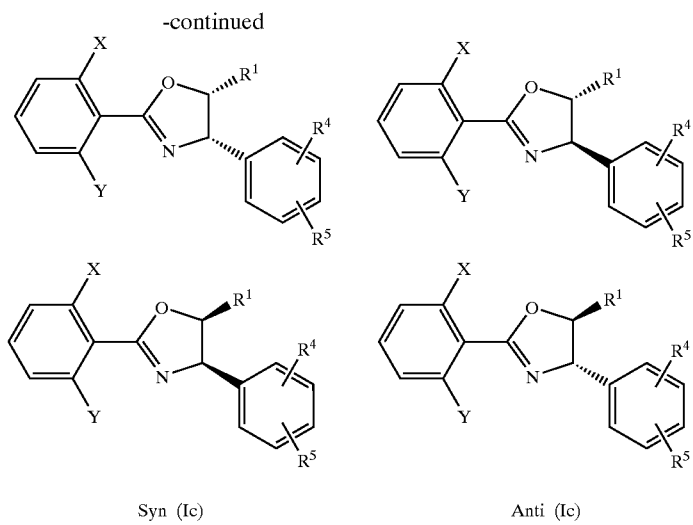

Syn (Ic)    Anti (Ic)

wherein $R^1$, Q, $R^4$, $R^5$, X and Y are as defined in formula (I).

In step a of Scheme B, oxazoline of formula Syn (Ib)/Anti (Ib) is reacted under standard Suzuki coupling reaction conditions with an appropriately substituted $R^5$-boronic acid to provide the product of formula Syn (Ic)/Anti (Ic) which can be separated using chromatographic techniques. The coupling reaction is carried out in an acetonitrile/water mixture, or ethanol, at a temperature in the range from ambient to refluxing temperature. Catalytic amounts of dichlorobis(triphenylphosphine)palladium(II) or tetrakis (triphenylphosphine)palladium(O) are typically used for coupling, however other Pd(II) or Pd(O) catalysts can also be used. Typically sodium carbonate was used as base in the coupling reaction but other inorganic or organic bases such as potassium carbonate or triethylamine can also be used.

Alternatively, compounds of formula (I), in particular racemic Syn (I) and Anti (I) can be prepared by the method illustrated in Scheme C:

Scheme C

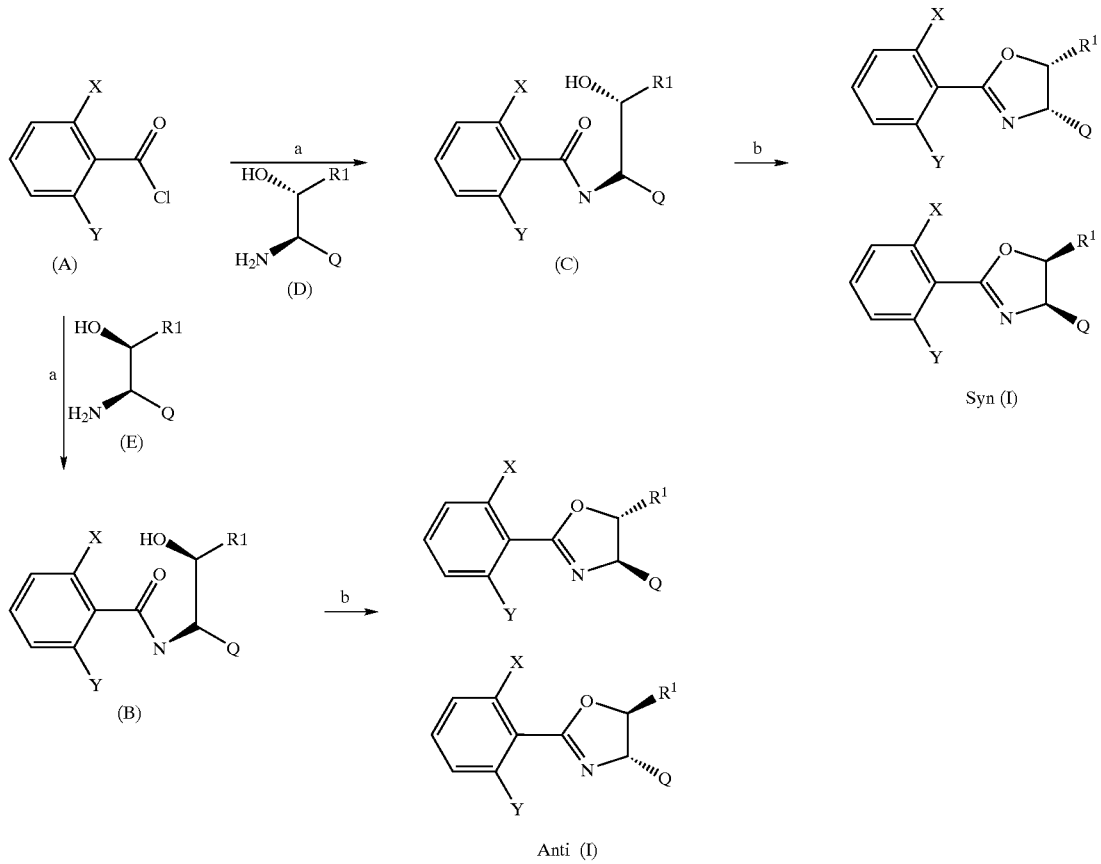

wherein R¹, Q, X and Y are as defined in formula (I).

In step a of Scheme C, the compound of formula (A) is reacted with an aminoalcohol (D) or (E) to afford a compound of formula (C) or (B). 1,2-Dichloroethane is the preferred solvent, however other polar aprotic solvents such as pyridine or THF can also be used.

The ring closure step b of Scheme C is similar to step b of Scheme A and provides the products of formula Syn (I) and Anti (I) which can be separated using chromatographic techniques.

Alternatively, when Q represents

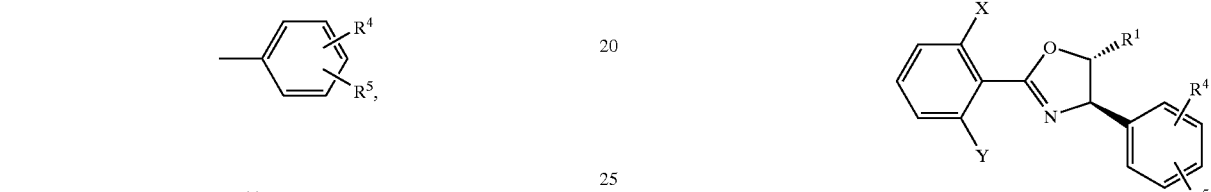

compounds of formula (I), in particular diastereomers Syn (Ic) and Anti (Ic), can be prepared by the method shown in Scheme D:

Scheme D

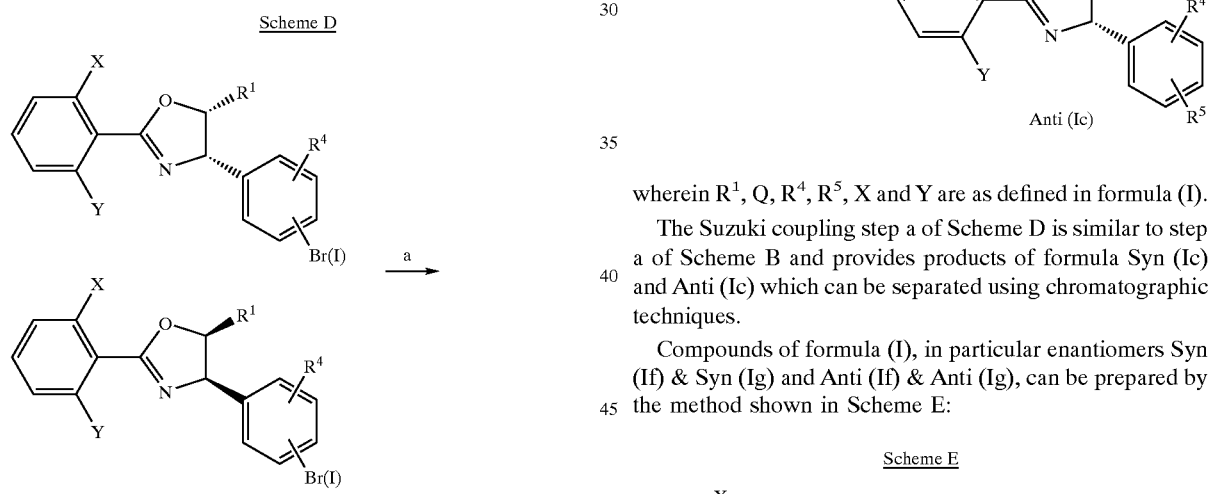

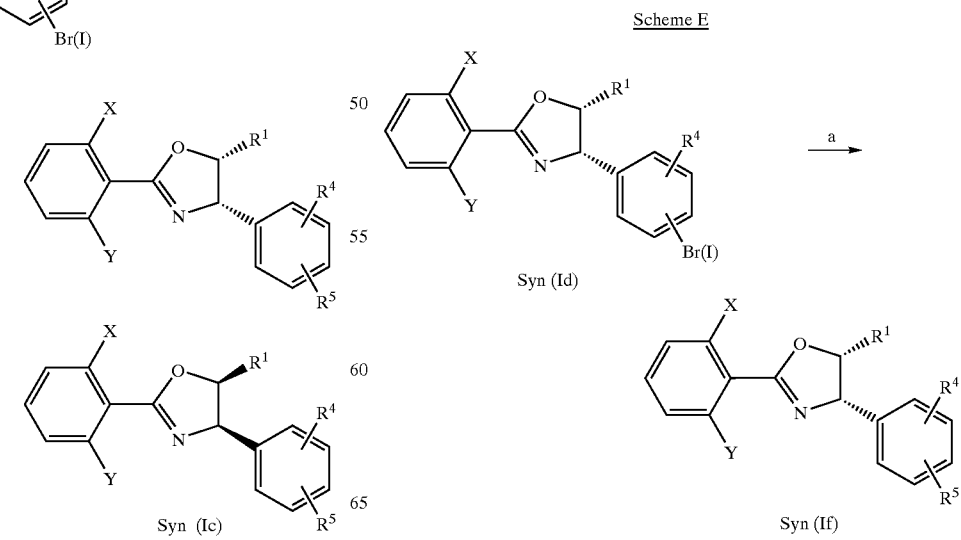

wherein R¹, Q, R⁴, R⁵, X and Y are as defined in formula (I).

The Suzuki coupling step a of Scheme D is similar to step a of Scheme B and provides products of formula Syn (Ic) and Anti (Ic) which can be separated using chromatographic techniques.

Compounds of formula (I), in particular enantiomers Syn (If) & Syn (Ig) and Anti (If) & Anti (Ig), can be prepared by the method shown in Scheme E:

Scheme E

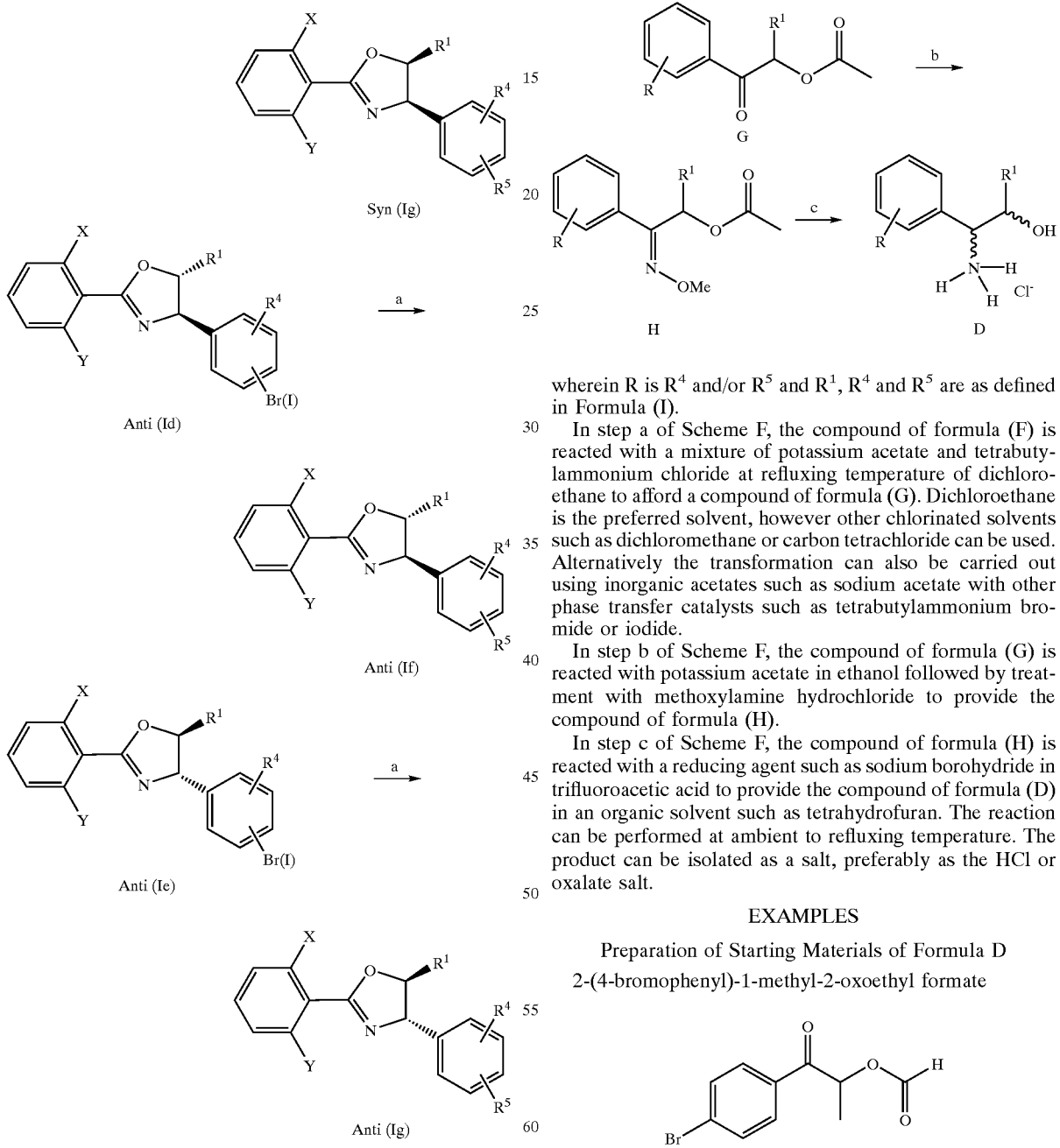

wherein $R^1$, Q, $R^4$, $R^5$, X and Y are as defined in formula (I).

The Suzuki coupling step a of Scheme E is similar to step a of Scheme B and provides products of formula Syn (If) & Syn (Ig) and Anti (If) & Anti (Ig) which can be purified using chromatographic techniques.

Compounds of formula (D) can be prepared by the method illustrated in Scheme F:

Scheme F wherein R is $R^4$ and/or $R^5$ and $R^1$, $R^4$ and $R^5$ are as defined in Formula (I).

In step a of Scheme F, the compound of formula (F) is reacted with a mixture of potassium acetate and tetrabutylammonium chloride at refluxing temperature of dichloroethane to afford a compound of formula (G). Dichloroethane is the preferred solvent, however other chlorinated solvents such as dichloromethane or carbon tetrachloride can be used. Alternatively the transformation can also be carried out using inorganic acetates such as sodium acetate with other phase transfer catalysts such as tetrabutylammonium bromide or iodide.

In step b of Scheme F, the compound of formula (G) is reacted with potassium acetate in ethanol followed by treatment with methoxylamine hydrochloride to provide the compound of formula (H).

In step c of Scheme F, the compound of formula (H) is reacted with a reducing agent such as sodium borohydride in trifluoroacetic acid to provide the compound of formula (D) in an organic solvent such as tetrahydrofuran. The reaction can be performed at ambient to refluxing temperature. The product can be isolated as a salt, preferably as the HCl or oxalate salt.

EXAMPLES

Preparation of Starting Materials of Formula D 2-(4-bromophenyl)-1-methyl-2-oxoethyl formate

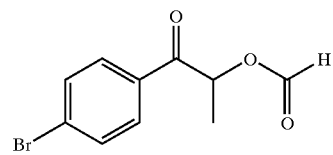

A 3.0-liter flask equipped with a mechanical stirrer, nitrogen inlet, thermocouple, and an addition funnel was charged with 2,4'-dibromopropiophenone (255 g, 0.873 mol), formic acid (97 g, 2.107 mol) and acetonitrile (1100 mL). The solution was cooled to 7° C. Triethylamine (194 g, 1.917 mol) was added via the addition funnel dropwise over 30 minutes keeping the temperature less than 15° C. The ice bath was removed, and the reaction mixture was stirred at 25° C. for 30 minutes. The triethylamine salts were filtered and rinsed with diethyl ether (100 mL). The filtrate was concentrated to approximately 700 mL volume. Diethyl ether (1000 mL) was added and the salts were removed by filtration. The filtrate was washed with water (100 mL), 0.1 N aq HCl (100 mL) and brine (100 mL). The organic layer was dried over sodium sulfate and then the solvent was removed under reduced pressure to give the product (213 g, 95%) as a white solid: mp 36–38° C.; $^1$H NMR (CDCl$_3$) 8.14 (s, 1H), 7.80 (d, 2H, J=8.8 Hz), 7.64 (d, 2H, J=8.8 Hz), 6.03 (q, 1H, J=7.0 Hz), 1.56 (d, 3H, J=7.0 Hz).

1-(4-bromophenyl)-2-hydroxypropan-1-one and 1-(4-bromophenyl)-1-hydroxypropan-2-one
Method 1

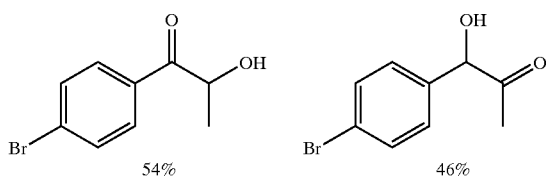

A 500 mL flask equipped with a mechanical stirrer, nitrogen inlet, thermocouple, and an addition funnel was charged with 2,4'-dibromopropiophenone (25.3 g, 0.087 mol), formic acid (8.4 g, 0.182 mol) and acetonitrile (110 mL). The solution was cooled to 10° C. Triethylamine (17.5 g, 0.173 mol) was added via the addition funnel dropwise over 30 minutes keeping the temperature less than 15° C. The ice bath was removed and the reaction mixture was stirred at 25° C. for 30 minutes. Concentrated HCl (35 mL) and water (20 mL) were added and the reaction mixture was stirred at 25° C. for 18 hours. Satd aq NH$_4$Cl (200 mL) was added and the product oiled out of the solution. The phases were separated, and the aqueous layer was extracted with dichloromethane (2×200 mL). The combined organic extracts were washed with brine and dried over sodium sulfate. The solvent was removed under reduced pressure to give the product (19.4 g, 97%) as an oil. The product is a 54:46 mixture of keto-alcohol isomers resulting from a keto-enol isomerization process. 1-(4-bromophenyl)-2-hydroxypropan-1-one: $^1$H NMR (CDCl$_3$) δ 7.79 (d, 2H, J=8.4 Hz), 7.65 (d, 2H, J=8.8 Hz), 5.10 (dq, 1H, J=7.0, 6.0 Hz), 3.73 (d, 1H, J=6.0 Hz), 1.44 (d, 3H, J=7.0 Hz). The minor isomer was 1-(4-bromophenyl)-1-hydroxypropan-2-one: $^1$H NMR (CDCl$_3$) δ 7.52 (d, 2H, J=8.4 Hz), 7.21 (d, 2H, J=8.4 Hz), 5.02 (d, 1H, J=4.0 Hz), 4.29 (d, 1H, J=4.0 Hz), 2.04 (s, 3H).
Method 2

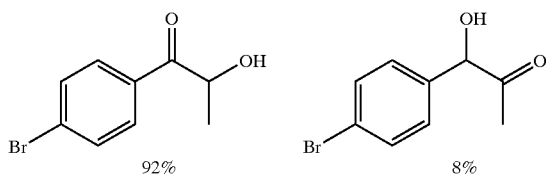

A 500 mL flask equipped with a mechanical stirrer, nitrogen inlet, thermocouple, and an addition funnel was charged with 2,4'-dibromopropiophenone (253 g, 0.866 mol), formic acid (84 g, 1.82 mol) and acetonitrile (1110 mL). The solution was cooled to 10° C. Triethylamine (175 g, 1.73 mol) was added via the addition funnel dropwise over 30 minutes keeping the temperature less than 15° C. The ice bath was removed and the reaction mixture was stirred at 25° C. for 30 minutes. Concentrated HCl (350 mL) and water (200 mL) were added and the reaction mixture was stirred at 25° C. for 3.5 hours. Satd aq NH$_4$Cl (200 mL) was added and the product oiled out of the solution. The phases were separated, and the aqueous layer was extracted with dichloromethane (2×200 mL). The combined organic extracts were washed with brine and dried over sodium sulfate. The solvent was removed under reduced pressure to give the product (193 g, 97%) as an oil. The product is a 92:8 mixture of keto-alcohol isomers resulting from a keto-enol isomerization process. 1-(4-bromophenyl)-2-hydroxypropan-1-one: $^1$H NMR (CDCl$_3$) δ 7.79 (d, 2H, J=8.4 Hz), 7.65 (d, 2H, J=8.8 Hz), 5.10 (dq, 1H, J=7.0, 6.0 Hz), 3.73 (d, 1H, J=6.0 Hz), 1.44 (d, 3H, J=7.0 Hz). The minor isomer was 1-(4-bromophenyl)-1-hydroxypropan-2-one: $^1$H NMR (CDCl$_3$) δ 7.52 (d, 2H, J=8.4 Hz), 7.21 (d, 2H, J=8.4 Hz), 5.02 (d, 1H, J=4.0 Hz), 4.29 (d, 1H, J=4.0 Hz), 2.04 (s, 3H).
Method 3

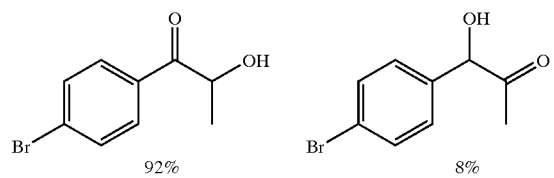

A 250 mL flask equipped with a magnetic stirrer, nitrogen inlet, and thermocouple was charged with 2-(4-bromophenyl)-1-methyl-2-oxoethyl formate (12.4 g, 0.048 mol) and methanol (100 mL). Potassium carbonate (2.0 g, 0.014 mol) was added and the reaction mixture was stirred at 28° C. for 1 hour. The methanol was removed under reduced pressure and the residue dissolved in diethyl ether (150 mL) and water (100 mL). The phases were separated, and the organic layer was washed with brine, dried over sodium sulfate, filtered and concentrated to give crude keto-alcohol (10.9 g, 98%) as a 92:8 mixture of isomeric keto-alcohols. 1-(4-bromophenyl)-2-hydroxypropan-1-one: $^1$H NMR (CDCl$_3$) δ 7.79 (d, 2H, J=8.4 Hz), 7.65 (d, 2H, J=8.8 Hz), 5.10 (dq, 1H, J=7.0, 6.0 Hz), 3.73 (d, 1H, J=6.0 Hz), 1.44 (d, 3H, J=7.0 Hz). The minor isomer was 1-(4-bromophenyl)-1-hydroxypropan-2-one: $^1$H NMR (CDCl$_3$) δ 7.52 (d, 2H, J=8.4 Hz), 7.21 (d, 2H, J=8.4 Hz), 5.02 (d, 1H, J=4.0 Hz), 4.29 (d, 1H, J=4.0 Hz), 2.04 (s, 3H).

(1E/Z)-1-(4-bromophenyl)-2-hydroxypropan-1-one O-methyl oxime and (2Z)-1-(4-bromophenyl)-1-hydroxypropan-2-one O-methyl oxime

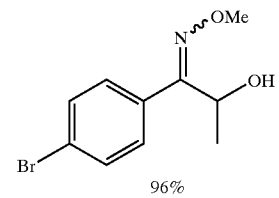

-continued

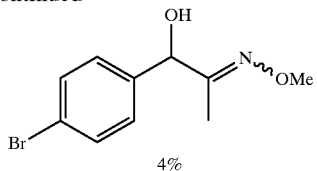

4%

A 3000 mL flask equipped with a mechanical stirrer, nitrogen inlet, and thermocouple was charged with 2-(4-bromophenyl)-1-methyl-2-oxoethyl formate (353 g, 1.37 mol) and ethanol (1500 mL). Potassium carbonate (19.0 g, 0.137 mol) was added and the reaction mixture was stirred at 28° C. for 2 hours. Methoxylamine hydrochloride (126 g, 1.51 mmol) and potassium acetate (148 g, 1.51 mmol) were added and the reaction mixture was stirred at 25° C. for 16 hours. The reaction mixture was filtered through Celite and concentrated to give a crude oil. This oil was dissolved into dichloromethane (600 mL) and washed with satd aq $NaHCO_3$ (3×500 mL) until the pH of the aqueous layer was >8.0. The organic layer was dried over $Na_2SO_4$, filtered, and concentrated to give crude product (314 g, 89%) as an oil and a 53/47 mixture of methoxime isomers of the desired regioisomer: $^1$H NMR (CDCl$_3$) δ 7.54 (d, 2H, J=8.4 Hz), 7.48* (m, 4H), 7.24 (d, 2H, J=8.4 Hz), 5.03* (dq, 1H, J=7.0, 4.8 Hz), 4.69 (dq, 1H, J=6.6, 4.8 Hz), 3.99* (s, 3H), 3.24* (d, 1H, J=8.4 Hz), 3.87 (s, 3H), 3.09 (d, 1H, J=4.8 Hz), 1.49* (d, 3H, J=7.0 Hz), 1.25 (d, 3H, J=6.6 Hz); EI/MS 258 m/e (M$^+$).

* minor isomer

The crude product also contained approximately 4% of the undesired regioisomeric methoxime-alcohol (2Z)-1-(4-bromophenyl)-1-hydroxypropan-2-one O-methyl oxime: $^1$H NMR (CDCl$_3$) δ 7.48 (m, 4H), 7.24 (d, 2H, J=8.4 Hz), 5.15 (d, 1H), 3.93 (s, 3H), 3.60 (d, 1H), 1.63 (s, 3H).

(1R,2R) and (1S,2S)-1-amino-1-(4-bromophenyl)propan-2-ol oxalate

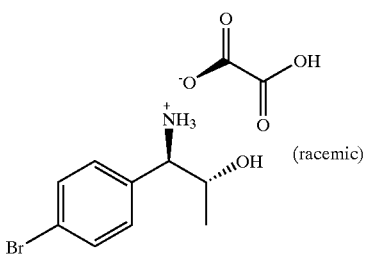

(racemic)

A 3000 mL round bottom flask equipped with a mechanical stirrer, addition funnel, thermocouple, and a reflux condenser was charged with NaBH$_4$ (66.0 g, 1.75 mole) and THF (900 mL). Trifluoroacetic acid (199.8 g, 135 mL, 1.75 mol) was placed into the addition funnel and slowly added (over one hour) to the NaBH$_4$ suspension keeping temperature less than 10° C. A solution of (1E/Z)-1-(4-bromophenyl)-2-hydroxypropan-1-one O-methyl oxime (150.1 g, 0.58 mol) in THF (100 mL) was added to the addition funnel, and then slowly (keeping temperature less than 50° C.) added to the trifluoroacetoxyborohydride suspension over 50 minutes. The reaction mixture was heated to 50° C. for 3.5 hours and then cooled to 25° C. The pH was adjusted to <3 by the careful addition of 2N HCl to neutralize the remaining NaBH$_4$. The mixture was stirred for 15 minutes at this pH. The pH of the mixture was then adjusted to >9 with 25% aq. NaOH. The reaction mixture was filtered and the THF removed under vacuum. The residue was dissolved into water (400 mL) and dichloromethane (200 mL), and the phases were separated. The aqueous layer was extracted with dichloromethane (5×200 mL). The organic extracts were washed with brine, dried over sodium sulfate, filtered, and the solvent was removed under reduced pressure to give crude product containing approximately 10–15% THF by weight. A 1000 mL round bottom flask equipped with a mechanical stirrer, thermometer, and nitrogen inlet was charged with crude 1-amino-2-hydroxy-1-(4-bromophenyl)propane (160 g, 0.556 mol) and methanol (550 mL). Oxalic acid (96.0 g, 1.07 mol) was added in one portion. The solution became cloudy and then cleared up as the temperature increased from 24° C. to 32° C. The product began to precipitate from the reaction mixture after 10 minutes. Stirring was continued until the reaction temperature returned to 25° C. (3 hours). The precipitate was filtered and the cake rinsed with dichloromethane (100 mL) to give the product (48.2 g, 27%) as a white solid: mp 199–200° C.; $^1$H NMR (DMSO-d$_6$) δ 7.62 (d, J=8.8 Hz, 2H), 7.42 (d, J=8.8 Hz, 2H), 7.15 (bs, 9H), 3.98–3.86 (m, 2H), 0.91 (d, J=5.9 Hz, 3H); $^{13}$C NMR (DMSO-d$_6$) δ 164.7, 135.7, 131.6, 130.2, 121.9, 67.7, 60.1, 20.1; Anal. Calcd. for $C_{11}H_{14}BrNO_5$: C, 41.27; H, 4.41; N, 4.38. Found: C, 41.10; H, 4.34; N, 4.26.

(1Z)-1-1-(4-bromophenyl)prop-1-enyl acetate

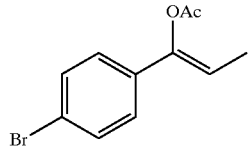

A 2000 mL round bottom flask equipped with a mechanical stirrer, nitrogen gas inlet, thermocouple, and a reflux condenser was charged with 4-bromopropiophenone (26.5 g, 124.4 mmol) and dimethyl sulfoxide (500 mL), and the mixture was cooled to 15° C. Sodium hydride (5.95 g, 149.3 mmol) was added portionwise over 30 minutes. The reaction mixture was warmed to 25° C. and was stirred for an additional 30 minutes. Acetic anhydride (14.0 g, 136.8 mmol) was added to the reaction mixture and the dark reddish brown solution became white with a large amount of salt precipitating from the solution. The reaction mixture was stirred until the reddish-brown color disappeared (15 minutes) and then water (1000 mL) was added. The aqueous solution was extracted with hexane (3×200 mL). The combined hexane extracts were washed with water (1000 mL) and then dried over sodium sulfate. The hexane was removed under reduced pressure to give the crude product (13.94 g, 43%, approximately 90% pure). A sample was purified by column chromatography to give product (3.94 g) as a white solid: mp 48–50° C.; $^1$H NMR (CDCl$_3$) δ 7.44 (d, 2H, J=8.4 Hz), 7.24 (d, 2H, J=8.4 Hz), 5.80 (q, 1H, J=7.0 Hz), 2.30 (s, 3H), 1.70 (d, 3H, J=7.0 Hz); EI/MS 255 m/e (M$^+$).

(2S,3S)-2-(4-bromophenyl)-3-methyloxiran-2-yl acetate

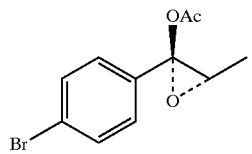

A 250 mL round bottom flask equipped with a magnetic stir bar, nitrogen gas inlet, thermocouple, and a reflux condenser was charged with (1Z)-1-1-(4-bromophenyl)prop-1-enyl acetate (1.0 g, 3.92 mmol), D-Epoxone (405 mg, 1.57 mmol), aqueous buffer (30 mL) and acetonitrile (50 mL), and the reaction mixture was cooled to 0° C. in an ice/water bath. The aqueous buffer was made by dissolving 1.91 g of borax and 16 mg of Na-EDTA into 100 mL water. A solution of Oxone (4.82 g, 7.84 mmol) in 30 mL of aqueous buffer was placed into a 30 mL syringe. A second syringe was charged with a solution of potassium carbonate (3.14 g, 22.74 mmol) in 30 mL water. The two syringes were placed into a syringe pump and the solutions were added to the reaction mixture over 1.5 hours keeping the temperature <5° C. The reaction mixture was warmed to 25° C. and sodium meta-bisulfite (1.0 g) was added to reduce excess oxidant (color of solution changed from blue to colorless). Satd aq NaCl (100 mL) was added, and the aqueous solution was extracted with hexane (3×100 mL). The combined hexane extracts were dried over sodium sulfate. The hexane was removed under reduced pressure to give the product as an oil (800 mg, 68%, 90% pure): $^1$H NMR (CDCl$_3$) δ 7.50 (d, 2H, J=8.8 Hz), 7.27 (d, 2H, J=8.4 Hz), 3.15 (q, 1H, J=5.5 Hz), 2.16 (s, 3H), 1.49 (d, 3H, J=5.5 Hz); EI/MS 271 m/e (M$^+$).

(2R)-1-(4-bromophenyl)-2-hydroxypropan-1-one

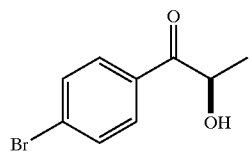

A 50 mL round bottom flask equipped with a magnetic stir bar, nitrogen gas inlet, and thermocouple was charged with (2S,3S)-2-(4-bromophenyl)-3-methyloxiran-2-yl acetate (490 mg, 1.81 mmol) and methanol (20 mL), and the reaction mixture was cooled to 0° C. in an ice/water bath. Potassium carbonate (15 mg, 0.1 mmol) was added, and the mixture was stirred at 0° C. for 3 hours. The reaction mixture was concentrated and purified by column chromatography to give the product as an oil (208 mg, 50%): $^1$H NMR (CDCl$_3$) δ 7.79 (d, 2H, J=8.4 Hz), 7.65 (d, 2H, J=8.8 Hz), 5.10 (q, 1H, J=7.0 Hz), 3.73 (bs, 1H), 1.44 (d, 3H, J=7.0Hz).

(1S)-2-(4-bromophenyl)-1-methyl-2-oxoethyl acetate

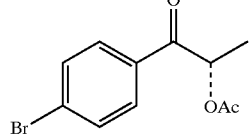

A 40 mL Parr bomb was charged with (2S,3S)-2-(4-bromophenyl)-3-methyloxiran-2-yl acetate (700 mg, 2.32 mmole) and was blanketed with nitrogen gas before closing. The heating block was pre-heated to 220° C. The Parr bomb was placed into the heating block for 35 minutes, then was removed from the heating block and cooled in ice. The Parr bomb was opened and the residue was dissolved into acetone (50 mL). The acetone was concentrated to give the crude product. Column chromatography gave the product (500 mg, 79%) as a yellow oil: $^1$H NMR (CDCl$_3$) δ 7.79 (d, 2H, J=8.4 Hz), 7.65 (d, 2H, J=8.8 Hz), 5.10 (q, 1H, J=7.0 Hz), 3.73 (bs, 1H), 1.44 (d, 3H, J=7.0 Hz); EI/MS 271 m/e (M$^+$).

(1E/Z,2R)-1-(4-bromophenyl)-2-hydroxypropan-1-one O-methyl oxime

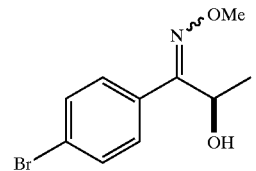

A 50 mL round bottom flask equipped with a magnetic stir bar, nitrogen gas inlet, and reflux condenser was charged with (2R)-1-(4-bromophenyl)-2-hydroxypropan-1-one (200 mg, 0.87 mmol), methoxylamine hydrochloride (88 mg, 1.05 mmol), potassium acetate (103 mg, 1.05 mmol) and ethanol (5 mL). The reaction mixture was heated to 78° C. for 3 hours. After cooling to 25° C. the reaction mixture was concentrated. Column chromatography gave the product (191 mg, 85%) as an oil and a 53/47 mixture of methoxime-isomers: $^1$H NMR (CDCl$_3$) δ 7.54 (d, 2H, J=8.4 Hz), 7.48* (m, 4H), 7.24 (d, 2H, J=8.4 Hz), 5.03* (dq, 1H, J=7.0, 4.8 Hz), 4.69 (dq, 1H, J=6.6, 4.8 Hz), 3.99* (s, 3H), 3.24* (d, 1H, J=8.4 Hz), 3.87 (s, 3H), 3.09 (d, 1H, J=4.8 Hz), 1.49* (d, 3H, J=7.0 Hz), 1.25 (d, 3H, J=6.6 Hz); EI/MS 258 m/e (M$^+$).

* minor isomer (1S,2E/Z)-2-(4-bromophenyl)-2-(methoxyimino)-1-methylethyl acetate

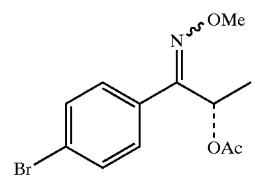

A 50 mL round bottom flask equipped with a magnetic stir bar, nitrogen gas inlet, and reflux condenser was charged with (1S)-2-(4-bromophenyl)-1-methyl-2-oxoethyl acetate (490 mg, 1.81 mmol), methoxylamine hydrochloride (181 mg, 2.17 mmol), potassium acetate (213 mg, 2.17 mmol) and ethanol (15 mL). The reaction mixture was heated to 78° C. for 7 hours. After cooling to 25° C. the reaction mixture was concentrated. Column chromatography gave the product (500 mg, 92%) as an oil and a 59/41 mixture of methoxime-isomers: $^1$H NMR (CDCl$_3$) δ 7.53 (d, 2H, J=8.4 Hz), 7.46* (m, 4H), 7.23 (d, 2H, J=8.4 Hz), 6.13 (q, 1H, J=7.0 Hz), 5.67* (q, 1H, J=6.6 Hz), 3.99 (s, 3H), 3.85* (s, 3H), 2.03* (s, 3H), 1.87 (s, 3H), 1.58 (d, 3H, J=7.0 Hz), 1.40* (d, 3H, J=6.6 Hz); EI/MS 300 m/e (M$^+$).

* minor isomer (2R)-1-amino-1(4-bromophenyl)propan-2-ol

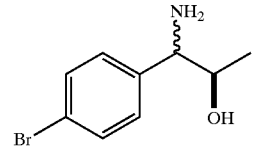

A 50 mL round bottom flask equipped with a magnetic stirrer, rubber septum, thermocouple, and a reflux condenser was charged with NaBH$_4$ (260 mg, 6.86 mmol) and THF (15 mL). Trifluoroacetic acid (782 mg, 0.53 mL, 6.86 mmol) was slowly added to the NaBH$_4$ suspension via a syringe through the rubber septum. Gas evolution occurred and the temperature increased to 27° C. from 23° C. A solution of (1E/Z,2R)-1-(4-bromophenyl)-2-hydroxypropan-1-one O-methyl oxime (590 mg, 2.28 mmol) in THF (5 mL) was slowly added to the reaction mixture. The reaction mixture was heated to 60° C. for 2 hours and then cooled to 25° C. The pH was adjusted to <3 by the careful addition of conc. HCl to neutralize the remaining NaBH₄. The pH was adjusted to >9 with 50% aq. NaOH. Water (50 mL) and dichloromethane (50 mL) were added and the phases were separated. The aqueous layer was extracted with dichloromethane (3×20 mL). The combined organic extracts were washed with brine (20 mL), dried over sodium sulfate, filtered, and concentrated under reduced pressure to give crude product as a waxy low-melting solid (480 mg, 91%, 50:50 mixture of 1-amino diastereomers): ¹H NMR (CDCl₃) δ 7.46* (d, 4H, J=8.4 Hz), 7.22 (d, 2H, J=8.4 Hz), 7.15 (d, 2H, J=8.4 Hz), 3.90 (m, 2H), 3.71 (m, 1H), 3.55 (d, 1H, J=7.7 Hz), 2.09 (bs, 3H), 1.04* (d, 3H, J=2.2 Hz), 1.02 (d, 3H, J=2.2 Hz).

2-(4-bromo-2-methylphenyl)-1-methyl-2-oxoethyl acetate

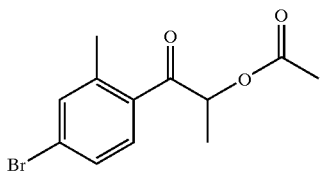

To a suspension of AlCl₃ (20.4 g, 153 mmol) in dichloroethane (150 mL, DCE) was added 2-bromopropionyl chloride, freshly prepared from 2-bromopropionic acid (23.4 g, 153 mmol), excess thionyl chloride, and catalytic N,N-dimethylformamide, at 25° C. To the resulting mixture was added 3-bromotoluene (20.2 g, 118 mmol) at 17° C., and the dark solution was stirred at room temperature for 2 h. The reaction was cooled to 0° C. and satd aq NH₄Cl was slowly added. The phases were separated and the organic layer was washed with additional satd aq NH₄Cl, dried (Na₂SO₄), filtered, and concentrated in vacuo to give crude 2-bromo-1-(4-bromo-2-methylphenyl)propan-1-one as a dark oil. Flash chromatography (SiO₂; 0–5% Et₂O/Hexanes) afforded the desired product as the major component in a mixture of isomeric products (32.3 g crude). The resulting gold oil (10.0 g, 32.7 mmol) was dissolved in 1,2-dichloroethane (120 mL), and potassium acetate (4.8 g, 49 mmol) and benzyltriethylammonium chloride (0.37 g, 1.6 mmol) were added. The resulting mixture was heated to reflux and stirred for 6 h and then at 25° C. for 16 h. The reaction mixture was washed with water, and the organic phase was dried (Na₂SO₄), filtered, and concentrated in vacuo to give crude product as a yellow oil. Flash chromatography (SiO₂; 0–20% Et₂O/Hexanes) afforded the racemic product (5.0 g, 54%) as a yellow oil: ¹H NMR (CDCl₃) δ 1.42 (d, 3H, J=7.3 Hz), 2.11 (s, 3H), 2.41 (s, 3H), 5.69 (q, 1H, J=7.3 Hz), 7.38–7.44 (m, 2H), 7.52 (d, 1H, J=8.4 Hz); EI/MS 285 m/e (M⁺).

N-[(1R,2R)- and (1S,2S)-1-(4-bromo-2-methylphenyl)-2-hydroxypropyl]-2,6-difluorobenzamide (Anti)
And
N-[(1R,2S)- and (1S,2R)-1-(4-bromo-2-methylphenyl)-2-hydroxypropyl]-2,6-difluorobenzamide (Syn):

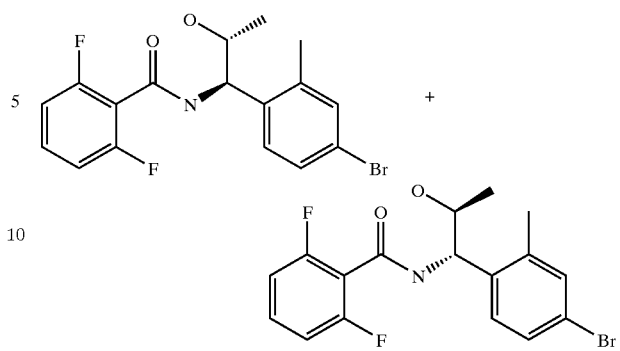

Racemic Mixtures of Syn and Anti

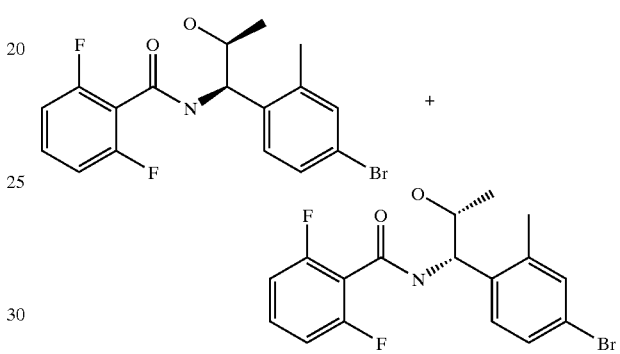

To a mixture of 2-(4-bromo-2-methylphenyl)-1-methyl-2-oxoethyl acetate (5.0 g, 17.5 mmol) and KOAc (2.75 g, 28.0 mmol) in EtOH (90 mL) was added methoxylamine hydrochloride (2.34 g, 28.0 mmol) and the resulting milky suspension was stirred at 70° C. for 4 h. An additional 0.5 equivalents of KOAc and methoxylamine hydrochloride were added and the reaction mixture was stirred at 70° C. for 8 h. The reaction mixture was diluted with water, and the EtOH was removed under reduced pressure. The aqueous residue was extracted with diethyl ether (2×75 mL), and the ether extracts were combined, washed with aq. NaHCO₃ and brine, dried (Na₂SO₄), filtered, and concentrated in vacuo to give 2-(4-bromo-2-methylphenyl)-2-(methoxyimino)-1-methylethyl acetate (5.0 g, 91%) as a racemic mixture of the E- and Z-methoxime isomers as a gold oil.

To a suspension of NaBH₄ (2.39 g, 63.3 mmol) in THF (50 mL) was added dropwise trifluoroacetic acid (7.21 g, 63.3 mmol) at a rate which maintained the reaction temperature between 19 and 30° C., and the resulting slurry was stirred at 25° C. for 30 minutes. To the trifluoroacetoxyborohydride suspension was added a solution of 2-(4-bromo-2-methylphenyl)-2-(methoxyimino)-1-methylethyl acetate (4.97 g, 15.8 mmol) in THF (15 mL). The resulting light yellow mixture was stirred at reflux for 3 h and then at 25° C. for 16 h. An additional 2 equivalents of the trifluoroacetoxyborohydride reducing agent was prepared and was added to the reaction at 25° C. The reaction was heated to reflux and stirred for 4 h. The excess NaBH₄ was neutralized by the careful addition of conc. HCl (pH<3). The pH was adjusted to >9 with 50% aq. NaOH and the alkaline mixture was diluted with water (100 mL). The THF was concentrated and the aqueous residue was extracted with CH₂Cl₂ (2×75 mL). The organic extracts were washed with brine, dried (Na₂SO₄), filtered, and concentrated in vacuo to give crude product as a gold oil. The oil was dissolved in CH$_2$Cl$_2$ and anhydrous HCl (g) was bubbled into the solution. The resulting HCl salt was collected by vacuum filtration and dried to give a diastereomeric mixture (60:40) of the desired product as a white solid (3 crops, 1.68 g, 38%).

To a suspension of 1-(4-bromo-2-methylphenyl)-2-hydroxyprop-1-aminium chloride (2.7 g, 9.6 mmol) in THF (90 mL) was added dropwise triethylamine (2.4 g, 24 mmol) at 0° C. To the resulting light yellow slurry was added dropwise a solution of 2,6-difluorobenzoyl chloride (1.7 g, 9.6 mmol) and the resulting light yellow slurry was warmed to 25° C. and stirred for 16 h. The reaction mixture was diluted with water and the THF was removed in vacuo. The aqueous residue was extracted with CH$_2$Cl$_2$ (2×100 mL), and the combined organic extracts were washed with 2 N HCl and brine, dried (Na$_2$SO$_4$), filtered, and concentrated in vacuo to give the crude product as a yellow solid. Flash chromatography (SiO$_2$; 0–5% Acetone/Hexanes) afforded both the anti (0.9 g, 24%) and syn (1.78 g, 48%) racemates as white solids. Anti: mp 184–186° C.; $^1$H NMR (CDCl$_3$) δ 1.36 (d, 3H, J=6.6 Hz), 1.86 (d, 1H, J=4.0 Hz), 2.43 (s, 3H), 4.02–4.07 (m, 1H), 5.26 (dd, 1H, J=2.8, 8.0 Hz), 6.86 (d, 1H, J=8.0 Hz), 6.96 (t, 2H, J=8.2 Hz), 7.19 (d, 1H, J=8.4 Hz), 7.32–7.44 (m, 3H); EI/MS 384 m/e (M$^+$).

Syn: mp 158–160° C.; $^1$H NMR (CDCl$_3$) δ 1.16 (d, 3H, J=6.2 Hz), 1.87 (d, 1H, J=6.2 Hz), 2.48 (s, 3H), 4.18–4.24 (m, 1H), 5.31–5.35 (m, 1H), 6.86 (d, 1H, J=7.7 Hz), 6.93 (t, 2H, J=8.2 Hz), 7.25–7.41 (m, 5H); EI/MS 384 m/e (M$^+$).

Preparation of Amidealcohol of Formula (C) and Preparation of Dihydrooxazoles of Formula (I)

N-[(1R,2R)- and (1S,2S)-1-(4-iodophenyl)-2-hydroxypropyl]-2,6-difluorobenzamide (Anti)

And

N-[(1R,2S)- and (1S,2R)-1-(4-iodophenyl)-2-hydroxypropyl]-2,6-difluorobenzamide (Syn)

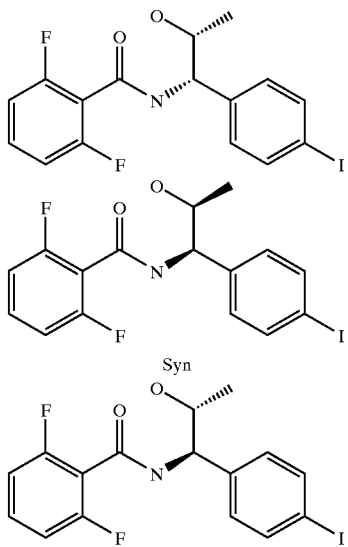

Syn

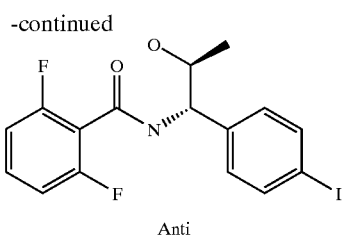

Anti

The amino alcohol (1.18 g, 3.8 mmol) was suspended in dry tetrahydrofuran (5.5 mL) and cooled to 3° C. Dry triethylamine (1.26 mL, 0.91 g, 9 mmol) was added followed by the acid chloride (0.66 g, 3.8 mmol) at a dropwise rate over 5 minutes. The reaction was allowed to proceed in the ice bath for 30 minutes and then for 16 h at 25° C. before being diluted with methylene chloride (20 mL) and water (20 mL). The organic layer was collected and the aqueous layer was extracted with methylene chloride (2×10 mL). The combined organic extracts were washed with water (30 mL), dilute hydrochloric acid (0.5 M, 2×10 mL) and brine (20 mL), dried over magnesium sulfate, and concentrated. Column chromatography (gradient of ethyl acetate in hexane) provided both the Syn (0.43 g, 27%) and Anti (0.45 g, 29%) compounds as white solids.

Syn: mp 133–134° C.; $^1$H NMR(CDCl$_3$) δ 7.72 (d, 2H), 7.38 (m, 1H), 7.11 (d, 2H), 6.95 (t, 2H), 6.86 (br d, 1H), 5.04 (dd, 1H), 4.13 (m, 1H), 1.96 (br, 1H), 1.33 (d, 3H); EI/MS 418 m/e (M$^+$).

Anti: mp 188–189° C.; $^1$H NMR (CDCl$_3$) δ 7.70 (d, 2H), 7.37 (m, 1H), 7.13 (d, 2H), 6.98 (m, 2H), 5.03 (dd, 1H), 4.21 (m, 1H), 1.61 (d, 1H), 1.12 (d, 3H); EI/MS 418 m/e (M$^+$). Compound 1, (4R,5S)- and (4S,5R)-4-(4-iodophenyl)-2-(2,6-difluorophenyl)-5-methyl-4,5-dihydro-1,3-oxazole

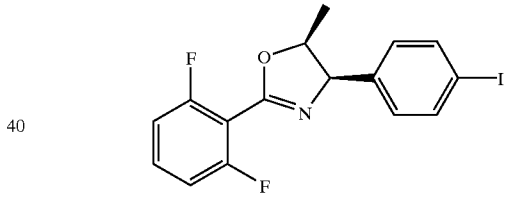

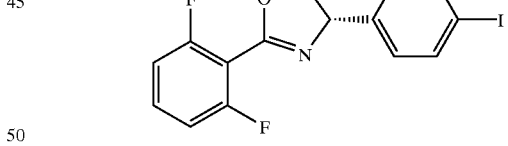

The amide alcohol (0.45 g, 1 mmol) was dissolved in methylene chloride (20 mL) and cooled to −78° C. (Diethylamino)sulfur trifluoride (0.14 mL, 0.17 g, 1 mmol) was added at a slow, dropwise rate, keeping the temperature below −65° C. The reaction was allowed to stir at −78° C. for one hour, left to warm to 25° C. over 16 hours and then poured into crushed ice (30 g) containing concentrated ammonia (5 mL). The organic layer was collected and the aqueous layer was extracted with methylene chloride (2×30 mL). The combined organic extracts were washed with water (50 mL), brine (50 mL) and dried over magnesium sulfate. Column chromatography (10:1 hexane/ethyl acetate) afforded the product (0.33 g, 77%) as a colorless gum: $^1$H NMR (CDCl$_3$) δ 7.70 (d, 2H), 7.43 (m, 1H), 7.07 (d, 2H), 7.02 (t, 2H), 4.87 (d, 1H), 4.56 (m, 1H), 1.57 (d, 3H); EI/MS 400 m/e (M$^+$).

Compound 2, (4R,5S)- and (4S,5R)-4-(4-bromophenyl)-2-(2,6-difluorophenyl)-5-methyl-4,5-dihydro-1,3-oxazole

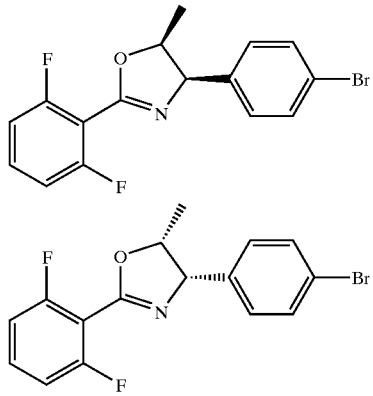

A 50 mL round bottom flask equipped with a stir bar, thermocouple, and a nitrogen inlet was charged with (1R, 2R)- and (1S,2S)-1-amino-1-(4-bromophenyl)-propan-2-ol oxalate (1.12 g, 3.5 mmol), triethylamine (1.13 g, 1.56 mL, 11.2 mmol) and dichloromethane (20 mL). After cooling the reaction mixture to 10° C., 2,6-difluorobenzoyl chloride (0.74 g, 4.2 mmol) was added keeping the temperature <25° C., and the reaction mixture was stirred for 30 min. 0.5 M aq. HCl (20 mL) was added and the phases were separated. The organic layer was washed with satd aq NaHCO₃ (20 mL), dried over sodium sulfate and filtered into a 50 mL round bottom flask equipped with a magnetic stirrer, and nitrogen inlet. To this solution were added N,N-dimethylformamide (2 drops) and thionyl chloride (600 mg, 5.0 mmol) and the reaction mixture was stirred at 25–30° C. for 2 hours. Water (20 mL) was carefully added and the mixture was stirred for an additonal 5 minutes. The organic layer was separated, washed with satd aq. NaHCO₃ (2×20 mL), dried over sodium sulfate, filtered, and concentrated under reduced pressure to give the crude product. Purification by column chromatography gave the product (900 mg, 73%) as a white solid: mp 65–67° C.; ¹H NMR (CDCl₃) δ 7.50 (d, 2H, J=8.4 Hz), 7.43 (m, 1H), 7.16 (d, 2H, J=8.1 Hz), 7.03 (tm, 2H, J=8.4 Hz), 5.48 (d, 1H, J=9.9 Hz), 5.15 (m, 1H), 0.98 (d, 3H, J=6.6 Hz); EI/MS 352 m/e (M⁺).

Compounds 2 & 24

Compound 24, (4R,5R)- and (4S,5S)-4-(4-bromophenyl)-2-(2,6-difluorophenyl)-5-methyl-4,5-dihydro-1,3-oxazole

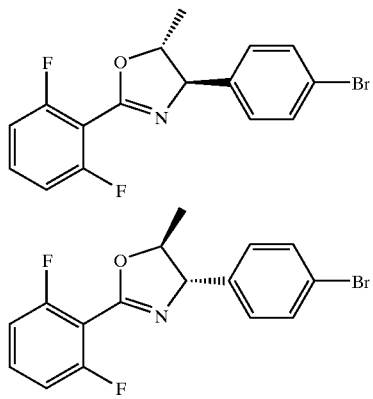

and

Compound 2, (4R,5S)- and (4S,5R)-4-(4-bromophenyl)-2-(2,6-difluorophenyl)-5-methyl-4,5-dihydro-1,3-oxazole

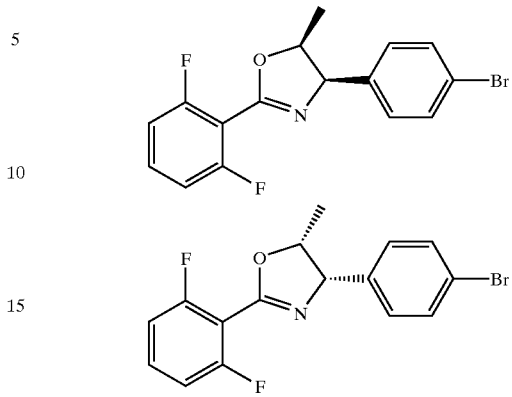

A 500 mL round bottom flask equipped with a stir bar, thermocouple, and a reflux condenser was charged with the crude 1-amino-1-(4-bromophenyl)propan-2-ol (10.0 g, 43.5 mmol), triethylamine (4.6 g, 6.1 mL, 45.0 mmol) and THF (100 mL). The reaction mixture was cooled to 10° C. 2,6-Difluorobenzoyl chloride (7.7 g, 5.5 mL, 43.5 mmol) was added to the THF solution keeping the temperature <30° C. The reaction mixture was stirred at 25–30° C. for 2 hours. Dichloromethane (40 mL) and water (60 mL) were added, and the phases were separated. The aqueous layer was extracted with dichloromethane (2×20 mL). The combined organic extracts were washed with aq. 0.5 N HCl (50 mL) and brine (50 mL), dried over sodium sulfate, filtered, and concentrated under reduced pressure to give crude amide product, which was placed in a 500 mL round bottom flask equipped with a stir bar, thermocouple, and a reflux condenser and charged with dichloromethane (250 mL). The reaction mixture was cooled to −78° C. (Diethylamino)sulfur trifluoride (6.31 g, 5.2 mL, 39.2 mmol) was added to the dichloromethane solution keeping the temperature <−70° C. The reaction mixture was allowed to warm to 25° C. while stirring over 16 h. The reaction mixture was poured into 100 g ice containing conc. ammonium hydroxide (10 mL). The phases were separated, and the aqueous layer was extracted with dichloromethane (2×100 mL). The combined organic extracts were washed with brine (100 mL), dried over sodium sulfate, filtered, and concentrated under reduced pressure to give crude product as a mixture of diastereomers, which were separated using column chromatography.

(4R,5S)- and (4S,5R)-4-(4-bromophenyl)-2-(2,6-difluorophenyl)-5-methyl-4,5-dihydro-1,3-oxazole. Compound 2 (86% purity)

Isolated as an off-white solid (23% yield): mp 55–57° C.; ¹H NMR (CDCl₃) δ 7.54–7.38 (m, 3H), 7.16 (d, J=8.42 Hz, 2H), 7.00 (t, J=8.42 Hz, 2H), 5.47 (d, J=9.89 Hz, 1H), 5.19–5.09 (m, 1H), 0.97 (d, J=5.86 Hz, 3H); EI/MS 352 m/e (M⁺).

(4R,5R)- and (4S,5S)-4-(4-bromophenyl)-2-(2,6-difluorophenyl)-5-methyl-4,5-dihydro-1,3-oxazole, Compound 24 (>98% purity)

Isolated as a tan solid solid (26% yield): mp 85–87° C.; ¹H NMR (CDCl₃) δ 7.51–7.28 (m, 3H), 7.20 (d, J=8.79 Hz, 2H), 6.99 (t, J=8.79, 8.06 Hz, 2H), 4.88 (d, J=6.96 Hz, 1H), 4.61–4.21 (p, 1H), 1.57 (d, J=6.23 Hz, 3H); EI/MS 352 m/e (M⁺).

Compound 3, (4R,5S)- and (4S,5R)-4-(4-bromophenyl)-2-(2-chloro-6-fluorophenyl)-5-methyl-4,5-dihydro-1,3-oxazole

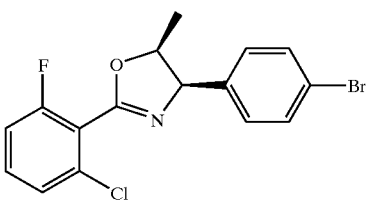

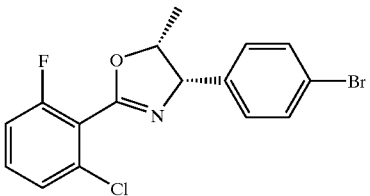

Isolated as a gummy solid (60% yield, two steps): $^1$H NMR (CDCl$_3$) δ 7.50 (dm, J=8.4 Hz, 2H), 7.36 (m, 1H), 7.28 (dm, J=9.9 Hz, 1H), 7.22 (dm, J=8.4 Hz, 2H), 7.10 (tm, J=8.4 Hz, 1H), 5.51 (d, J=9.9 Hz, 1H), 5.33 (m, 1H), 0.98 (d, J=6.2 Hz, 3H); EI/MS 368 m/e (M$^+$).

Compound 4, (4R,5S)- and (4S,5R)-2-(2-chloro-6-fluorophenyl)-5-methyl-4-[4'-(trifluoromethyl)-1,1'-biphenyl-4-yl]-4,5-dihydro-1,3-oxazole

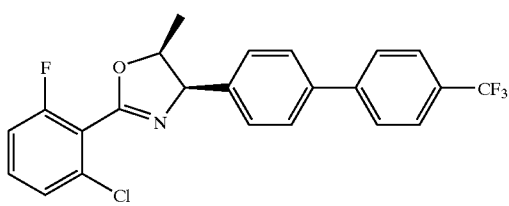

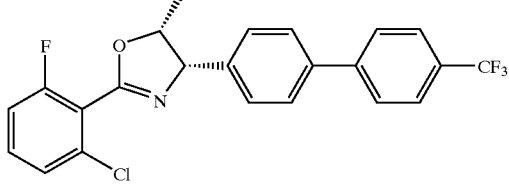

Isolated as a yellow solid (35% yield): mp 118–119° C.; $^1$H NMR (CDCl$_3$) δ 7.70 (m, 4H), 7.62 (d, J=8.1 Hz, 2H), 7.44 (d, J=8.1 Hz, 2H), 7.38 (m, 1H), 7.30 (d, J=8.1 Hz, 1H), 7.12 (t, J=8.8 Hz, 1H), 5.61 (d, J=9.9 Hz, 1H), 5.23 (m, 1H), 1.04 (d, J=6.6 Hz, 3H); ESI/MS 435 m/e (M+1); Anal. Calcd. for C$_{23}$H$_{16}$ClF$_4$NO: C, 63.68; H, 3.72; N, 3.23. Found: C, 63.16; H, 3.89; N, 3.40.

Compound 5, (4R,5S)- and 4S,5R)-2-(2,6-difluorophenyl)-5-methyl-4-[4'-(trifluoromethyl)-1,1'-biphenyl-4-yl]-4,5-dihydro-1,3-oxazole

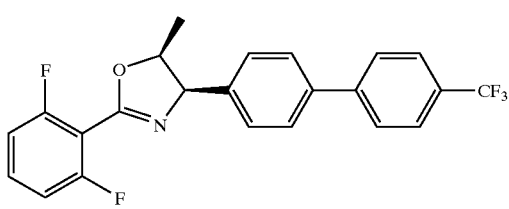

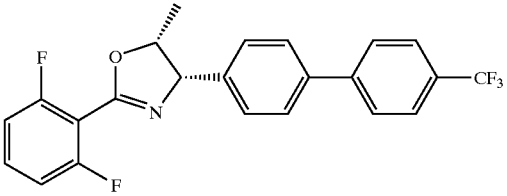

Isolated as an orange colored solid (52% yield): mp 105–106° C.; $^1$H NMR (CDCl$_3$) δ 7.70 (s, 4H), 7.64 (d, 1H), 7.44 (t, 1H), 7.39 (d, 2H), 7.02 (t, 2H), 5.56 (d, 1H), 5.17–5.24 (m, 1H), 1.04 (d, 3H); EI/MS 417 m/e (M$^+$).

Compound 6, (4S,5R)- and (4R,5S)-2-(2,6-difluorophenyl)-4-(4'-trifluoromethoxy-1,1'-biphenyl-4-yl)-5-methyl-4,5-dihydro-1,3-oxazole

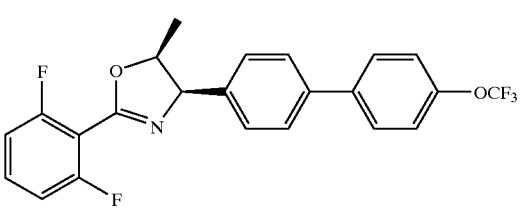

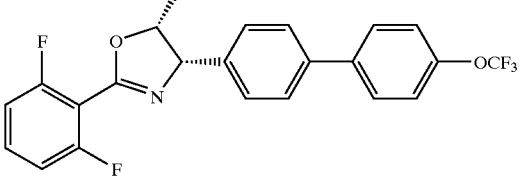

Isolated as a yellow solid (72% yield): mp 106–109° C.; $^1$H NMR (CDCl$_3$) δ 7.63–7.54 (m, 4H), 7.48–7.38 (m, 1H), 7.35 (d, 2H, J=8.4 Hz), 7.28 (d, 2H, J=8.4 Hz), 7.01 (t, 2H, J=8.1 Hz), 5.55 (d, 1H, J=9.9 Hz), 5.18 (m, 1H), 1.03 (d, 3H, J=6.6 Hz); EI/MS 433 m/e (M$^+$). *$^1$H NMR shows that sample is contaminated with approximately 5% of the anti-isomer (racemic).

Compound 7, (4S,5R)- and (4R,5S)-2-(2,6-difluorophenyl)-4-(4'-isopropyl-1,1'-biphenyl-4-yl)-5-methyl-4,5-dihydro-1,3-oxazole

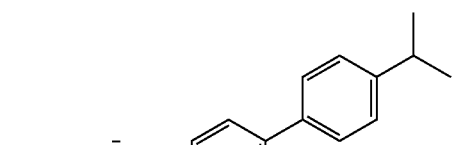

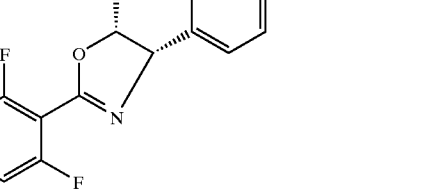

+

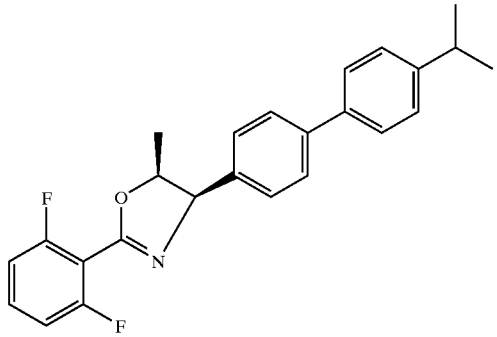

The Suzuki coupling parallel synthesis approach used to obtain the desired targets is as described for Compound 7.

To the reaction vessel were added (4R, 5S)- and (4S, 5R)-4-(4-bromophenyl)-2-(2,6-difluorophenyl)-5-methyl-4,5-dihydro-1,3-oxazole (0.25 g, 0.7 mmol), $Na_2CO_3$ (0.16 g, 1.5 mmol), 4-isopropylphenylboronic acid (0.15 g, 0.91 mmol). To the solid reagents were added 4 mL ethanol and tetrakis(triphenylphosphine)palladium(O) (0.08 g, 0.07 mmol), followed by 3 mL ethanol. With mechanical agitation, the reaction was heated to 72° C., and the resulting mixture was mechanically agitated for 16 h. The reaction was cooled to 25° C. and filtered. The solids were removed by filtration and washed with additional ethanol. The solvents were removed in vacuo, and the residue was dissolved in $CH_2Cl_2$. The solids were removed by filtration and the $CH_2Cl_2$ removed in vacuo. Preparative liquid chromatography afforded an off white oil (0.10 g, 38%): $^1H$ NMR ($CDCl_3$) δ 1.06 (d, 3H, J=6.6 Hz), 1.32 (d, 6H, J=7.0 Hz), 2.93–3.03 (m, 1H), 5.15–5.25 (m, 1H), 5.57 (d, 1H, J=9.9 Hz), 7.03 (t, 2H, J=8.0 Hz), 7.35 (t, 4H, J=8.4, 9.2 Hz), 7.41–7.51 (m, 1H), 7.55–7.66 (m, 4H); MS 392 m/e (M+).

Compound 8, (4S,5R)- and (4R,5S)-2-(2,6-difluorophenyl)-4-(3',4'-dimethyl-1,1'-biphenyl-4-yl)-5-methyl-4,5-dihydro-1,3-oxazole Isolated as an off-white solid (16% yield): mp 101–111° C.; $^1H$ NMR ($CDCl_3$) δ 1.03 (d, 3H, J=6.6 Hz), 2.32 (d, 6H, J=8.1 Hz), 5.13–5.23 (m, 1H), 5.54 (d, 1H, J=9.5 Hz), 7.01 (t, 2H, J=8.4, 8.1 Hz), 7.20 (d, 1H, J=7.7 Hz), 7.31 (d, 2H, J=8.4 Hz), 7.36–7.48 (m, 3H), 7.57 (d, 2H, J=8.1 Hz); MS 378 m/e (M+).

Compound 9, (4S,5R)- and (4R,5S)-2-(2,6-difluorophenyl)-5-methyl-4-(4'-methyl-1,1'-biphenyl-4-yl)-4,5-dihydro-1,3-oxazole

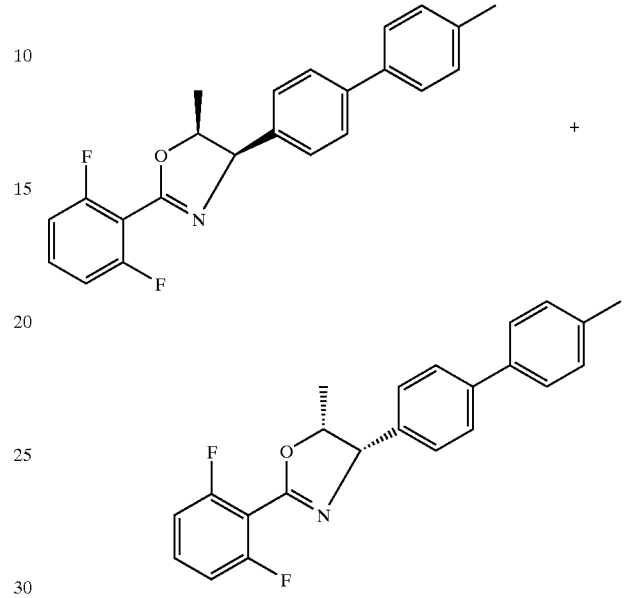

Isolated as a white solid (17% yield): mp 149–152° C.; $^1H$ NMR ($CDCl_3$) δ 1.03 (d, 3H, J=6.2 Hz), 2.40 (s, 3H), 5.15–5.21 (m, 1H), 5.54 (d, 1H, J=9.9 Hz), 7.01 (t, 2H, J=8.4, 8.1 Hz), 7.25 (d, 2H, J=8.1 Hz), 7.33 (d, 2H, J=8.1 Hz), 7.41–7.46 (m, 1H), 7.51 (d, 2H, J=8.1 Hz), 7.58 (d, 2H, J=8.4 Hz); MS 363 m/e (M+).

Compound 10, (4S,5R)- and (4R,5S)-4-(4'-chloro-1,1'-biphenyl-4-yl)-2-(2,6-difluorophenyl)-5-methyl-4,5-dihydro-1,3-oxazole

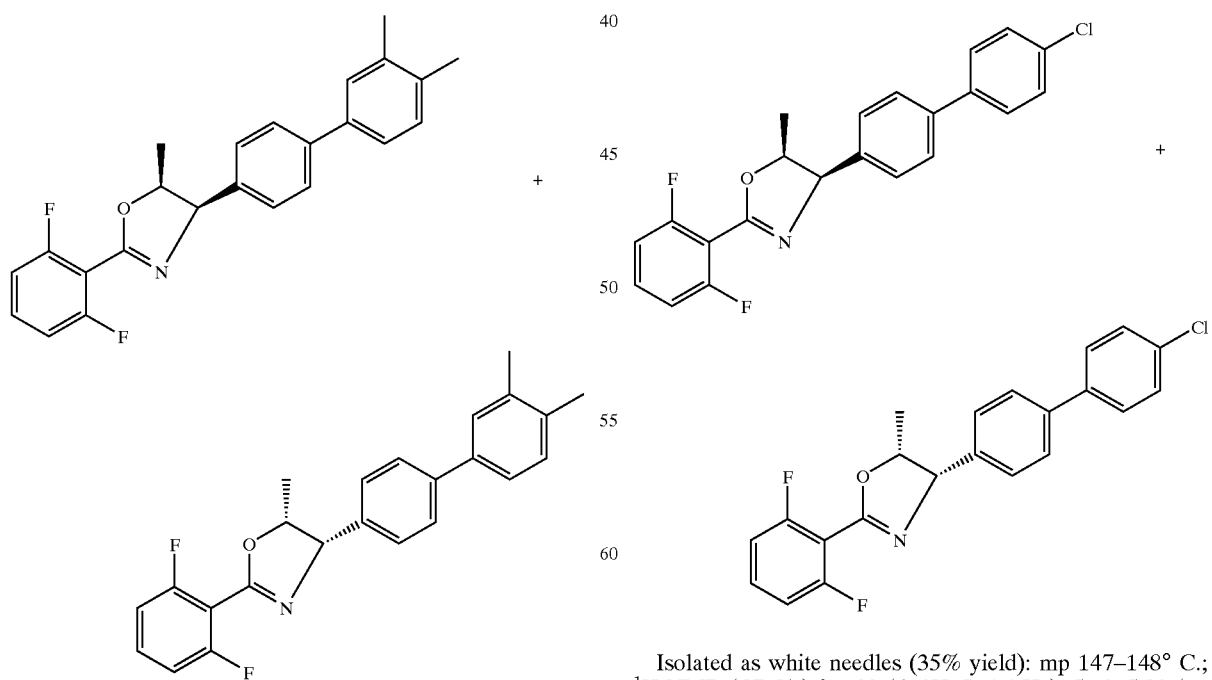

Isolated as white needles (35% yield): mp 147–148° C.; $^1H$ NMR ($CDCl_3$) δ 1.02 (d, 3H, J=6.6 Hz), 5.13–5.23 (m, 1H), 5.54 (d, 1H, J=9.9 Hz), 6.95–7.04 (m, 2H), 7.34–7.47 (m, 4H), 7.48–7.60 (m, 5H); MS 383 m/e (M+).

Compound 11, (4S,5R)- and (4R,5S)-2-(2,6-difluorophenyl)-5-methyl-4-[3'-(trifluoromethyl)-1,1'-biphenyl-4-yl]-4,5-dihydro-1,3-oxazole

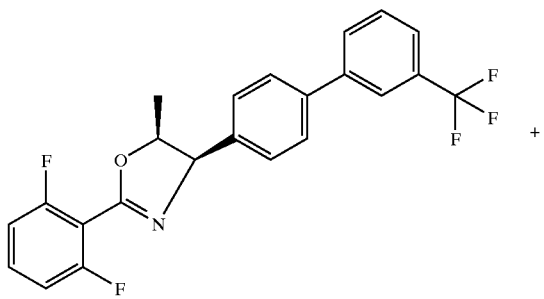

Isolated as a yellow glass (21% yield): ¹H NMR (CDCl₃) δ 1.04 (d, 3H, J=6.6 Hz), 5.17–5.24 (m, 1H), 5.57 (d, 1H, J=9.9 Hz), 6.98–7.05 (m, 2H), 7.32–7.49 (m, 3H), 7.51–7.67 (m, 4H), 7.70–7.85 (m, 2H); MS 418 m/e (M⁺).

Compound 12, (4R,5S)- and (4S,5R)-2-(2,6-difluorophenyl)-4-(4'-ethoxy-1,1'-biphenyl-4-yl)-5-methyl-4,5-dihydro-1,3-oxazole

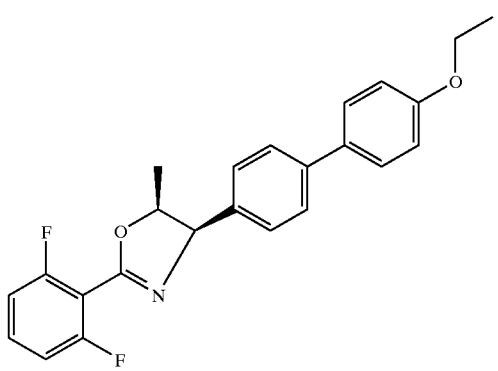

Isolated as white crystals (18% yield): mp 128–130° C.; ¹H NMR (CDCl₃) δ 1.03 (d, 3H, J=6.6 Hz), 1.44 (t, 3H, J=7.0 Hz), 4.08 (q, 2H, J=7.0 Hz), 5.12–5.22 (m, 1H), 5.53 (d, 1H, J=10.0 Hz), 6.95–7.04 (m, 4H), 7.31 (d, 2H, J=8.4 Hz), 7.38–7.50 (m, 1H), 7.51–7.59 (m, 4H); MS 393 m/e (M⁺).

Compound 13, (4R,5S)- and (4S,5R)-4-[4-(2,2-difluoro-1,3-benzodioxol-5-yl)phenyl]-2-(2,6-difluorophenyl)-5-methyl-4,5-dihydro-1,3-oxazole

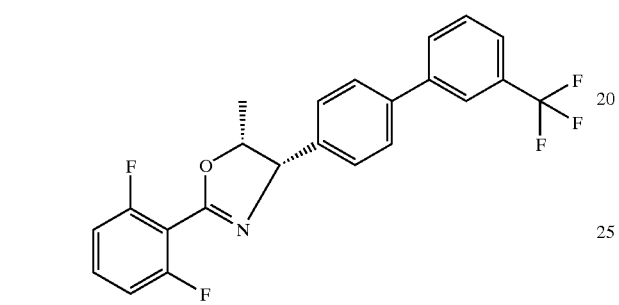

Isolated as white crystals (25% yield): mp 132–134° C.; ¹H NMR (CDCl₃) δ 1.04 (d, 3H, J=6.6 Hz), 5.17–5.25 (m, 1H), 5.56 (d, 1H, J=9.9 Hz), 6.98–7.05 (m, 3H), 7.12–7.18 (m, 1H), 7.29–7.32 (m, 1H), 7.39–7.52 (m, 3H), 7.70–7.74 (m, 2H); MS 430 m/e (M⁺).

Compound 14, (4R,5S)- and (4S,5R)-2-(2,6-difluorophenyl)-4-(4'-fluoro-1,1'-biphenyl-4-yl)-5-methyl-4,5-dihydro-1,3-oxazole

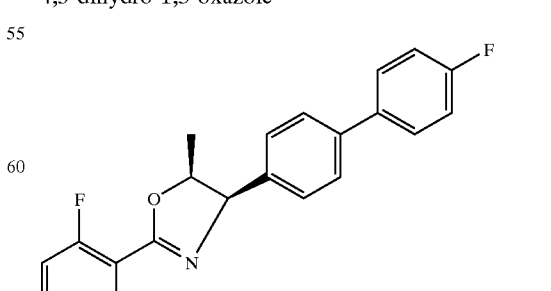

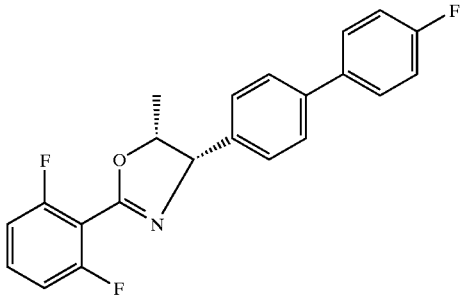

Isolated as a white solid (12% yield): mp 140–142° C.; $^1$H NMR (CDCl$_3$) δ 1.03 (d, 3H, J=6.6 Hz), 5.13–5.23 (m, 1H), 5.55 (d, 1H, J=9.9 Hz), 6.98–7.05 (m, 2H), 7.08–7.16 (m, 2H), 7.35 (d, 2H, J=8.4 Hz), 7.39–7.53 (m, 1H), 7.53–7.60 (m, 4H); MS 368 m/e (M$^+$).

Compound 15, (4R,5S)- and (4S,5R)-2-(2,6-difluorophenyl)-4-(2'-fluoro-1,1'-biphenyl-4-yl)-5-methyl-4,5-dihydro-1,3-oxazole

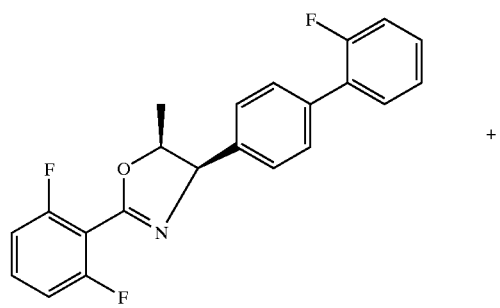

Isolated as a tan oil (13% yield): $^1$H NMR (CDCl$_3$) δ 1.04 (d, 3H, J=6.6 Hz), 5.14–5.24 (m, 1H), 5.55 (d, 1H, J=9.5 Hz), 6.95–7.07 (m, 2H), 7.11–7.25 (m, 3H), 7.27–7.52 (m, 4H), 7.55–7.60 (m, 2H); MS 368 m/e (M$^+$).

Compound 16, (4R,5S)- and (4S,5R)-2-(2,6-difluorophenyl)-4-[2'-fluoro-4'-(trifluoromethyl)-1,1'-biphenyl-4-yl]-5-methyl-4,5-dihydro-1,3-oxazole

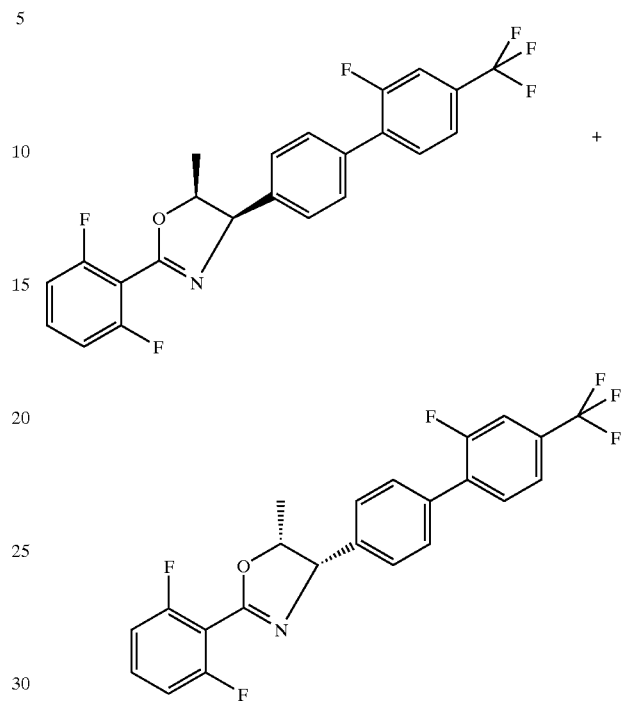

Isolated as a white solid (3% yield): mp 111–112° C.; $^1$H NMR (CDCl$_3$) δ 1.05 (d, 3H, J=6.6 Hz), 5.18–5.23 (m, 1H), 5.57 (d, 1H, J=9.9 Hz), 7.02 (t, 2H, J=8.1, 8.4 Hz), 7.38–7.50 (m, 5H), 7.56–7.61 (m, 3H); MS 436 m/e (M$^+$).

Compound 17, (4R,5S)- and (4S,5R)-4-(4-bromophenyl)-2-(2-methyl)-5-methyl-4,5-dihydro-1,3-oxazole

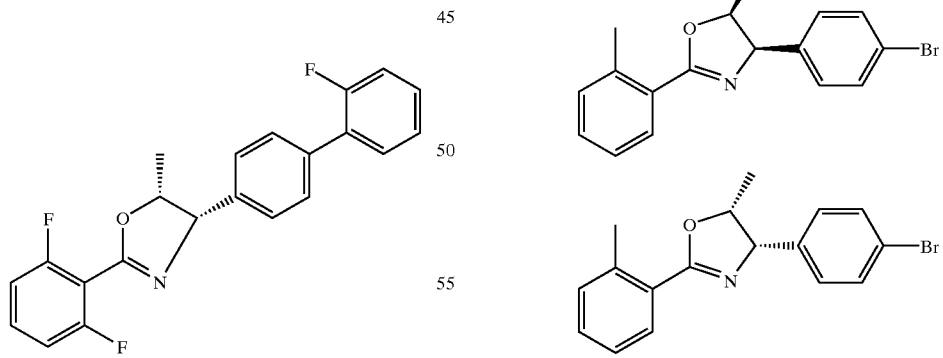

Isolated as a colorless oil (63% yield): $^1$H NMR (CDCl$_3$) δ 7.89 (d, J=7.7 Hz, 1H), 7.46 (dm, J=8.5 Hz, 2H), 7.37 (m, 1H), 7.25 (m, 2H), 7.13 (dm, J=8.2 Hz, 2H), 5.43 (d, J=9.6 Hz, 1H), 5.05 (m, 1H), 2.66 (s, 3H), 0.94 (d, J=6.6 Hz, 3H); EI/MS 330 m/e (M$^+$); Anal. Calcd. for C$_{17}$H$_{16}$BrNO: C, 61.83; H, 4.88; N, 4.24. Found: C, 61.75; H, 4.81; N, 4.31.

Compound 18, (4S,5R)- and (4R,5S)-5-methyl-2-(2-methylphenyl)-4-[4'-(trifluoromethoxy)-1,1'-biphenyl-4-yl]-4,5-dihydro-1,3-oxazole

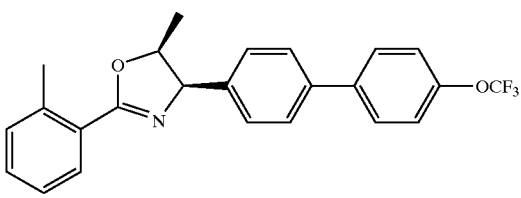

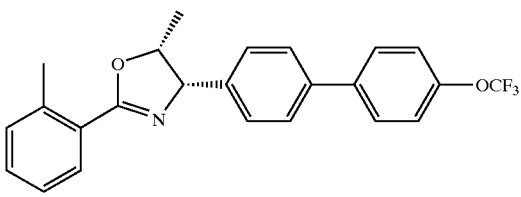

Isolated as a colorless oil (83% yield): $^1$H NMR (CDCl$_3$) δ 7.92 (d, J=8.1 Hz, 1H), 7.60 (dm, J=8.8 Hz, 2H), 7.54 (d, J=8.1 Hz, 2H), 7.40–7.24 (m, 7H), 5.52 (d, J=9.9 Hz, 1H), 5.10 (m, 1H), 2.69 (s, 3H), 1.01 (d, J=6.6 Hz, 3H); EI/MS 411 m/e (M$^+$).

Compound 19, (4R,5S)- and (4S,5R)-5-methyl-2-(2-methylphenyl)-4-[4'-(trifluoromethyl)-1,1'-biphenyl-4-yl]-4,5-dihydro-1,3-oxazole

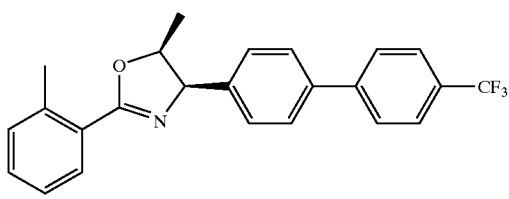

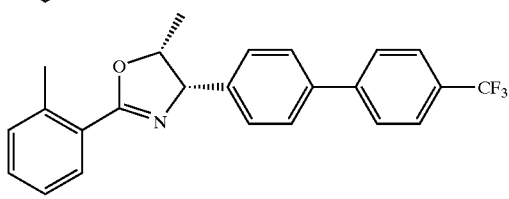

Isolated as a colorless oil (58% yield): $^1$H NMR (CDCl$_3$) δ 7.92 (d, J=7.7 Hz, 1H), 7.69 (s, 4H), 7.58 (dm, J=8.2 Hz, 2H), 7.41–7.34 (m, 3H), 7.28 (d, J=7.4 Hz, 2H), 5.53 (d, J=9.9 Hz, 1H), 5.11 (m, 1H), 2.70 (s, 3H), 1.01 (d, J=6.6 Hz, 3H); EI/MS 395 m/e (M$^+$).

Compound 20, (4R,5S)- and (4S,5R)-2-(2-chloro-6-fluorophenyl)-5-methyl-4-[4'-(trifluoromethoxy)-1,1'-biphenyl-4-yl]-4,5-dihydro-1,3-oxazole

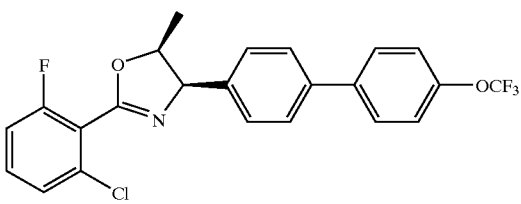

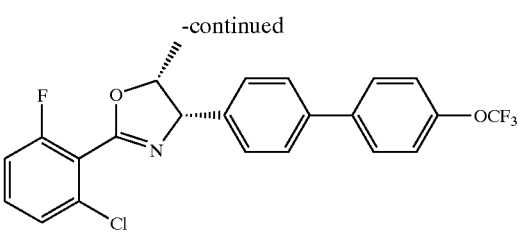

Isolated as a white solid (78% yield): mp 100–102° C.; $^1$H NMR (CDCl$_3$) δ 7.62 (d, J=8.8 Hz, 2H), 7.57 (d, J=8.8 Hz, 2H), 7.43–7.35 (m, 3H), 7.1–7.27 (m, 3H), 7.11 (tm, J=8.8 Hz, 1H), 5.60 (d, J=9.9 Hz, 1H), 5.22 (m, 1H), 1.04 (d, J=6.6 Hz, 3H); EI/MS 450 m/e (M$^+$); Anal. Calcd. for C$_{23}$H$_{16}$ClF$_4$NO$_2$: C, 61.41; H, 3.59; N, 3.11. Found: C, 61.17; H, 3.70; N, 3.02.

Compound 21, (4R,5S)- and (4S,5R)-2-(2-chloro-6-fluorophenyl)-4-(4'-ethoxy-1,1'-biphenyl-4-yl)-5-methyl-4,5-dihydro-1,3-oxazole

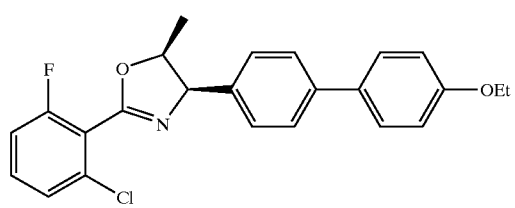

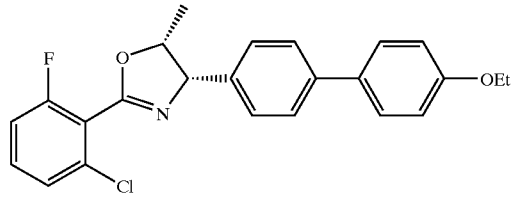

Isolated as a gummy oil (60% yield): $^1$H NMR (CDCl$_3$) δ 7.55 (m, 4H), 7.41–7.33 (m, 3H), 7.27 (d, J=8.8 Hz, 1H), 7.10 (tm, J=9.5 Hz, 1H), 6.96 (dm, J=8.8 Hz, 2H), 5.75 (d, J=9.9 Hz, 1H), 5.20 (m, 1H), 4.07 (q, J=7.0 Hz, 2H), 1.43 (t, J=7.0 Hz, 3H), 1.03 (d, J=6.6 Hz, 3H); ESI/MS 411 m/e (M+1).

Compound 22, (4R,5R)- and (4S,5S)-4-(4-iodophenyl)-2-(2,6-difluorophenyl)-5-methyl-4,5-dihydro-1,3-oxazole

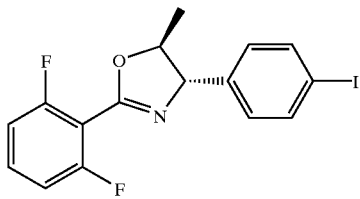

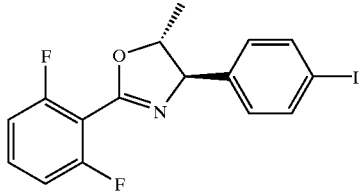

Isolated as a colorless liquid (88% yield): $^1$H NMR (CDCl$_3$) δ 7.69 (d, 2H), 7.43 (m, 1H), 6.96–7.05 (m, 4H), 5.45 (d, 1H), 5.09–5.19 (m, 1H), 0.97 (d, 3H); EI/MS 399 m/e (M$^+$).

Compound 23, (4R,5R)- and (4S,5S)-4-(4-bromophenyl)-2-(2-chloro-6-fluorophenyl)-5-methyl-4,5-dihydro-1,3-oxazole

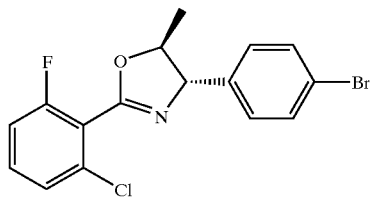

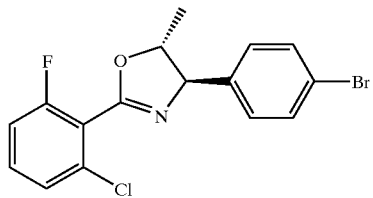

Isolated as a white solid (9% yield): mp 90–93° C.; $^1$H NMR (CDCl$_3$) δ 1.59 (d, J=6.2 Hz, 3H), 4.58–4.62 (m, 1H), 4.89–4.92 (d, J=7.0 Hz, 1H), 7.09 (m, 1H), 7.22–7.29 (m, 4H), 7.34–7.42 (m, 1H), 7.49–7.53 (m, 2H); EI/MS 325 m/e (M$^+$).

Compound 25, (4S,5S)- and (4R,5R)-2-(2,6-difluorophenyl)-4-(4'-fluoro-1,1'-biphenyl-4-yl)-5-methyl-4,5-dihydro-1,3-oxazole

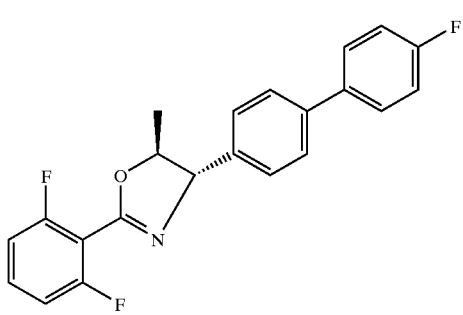

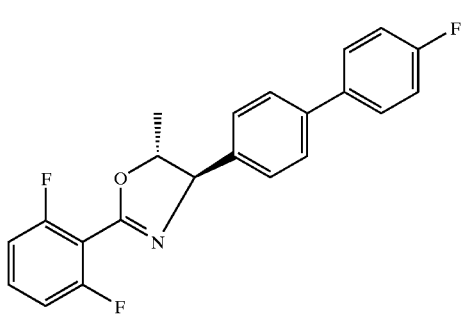

Isolated as brown crystals (45% yield): mp 126–128° C.; $^1$H NMR (CDCl$_3$) δ 1.61 (d, 3H, J=6.2 Hz), 4.62–4.71 (m, 1H), 4.97 (d, 1H, J=7.0 Hz), 6.96–7.04 (m, 2H), 7.09–7.15 (m, 2H), 7.38–7.48 (m, 3H), 7.51–7.56 (m, 4H); MS 368 m/e (M$^+$).

Compound 26, (4S,5S)- and (4R,5R)-2-(2,6-difluorophenyl)-5-methyl-4-[4'-(trifluoromethyl)-1,1'-biphenyl-4-yl]-4,5-dihydro-1,3-oxazole

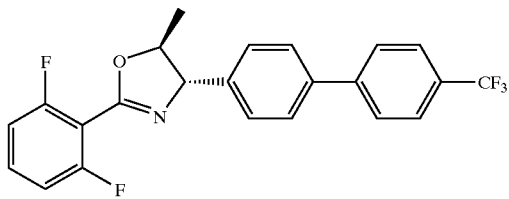

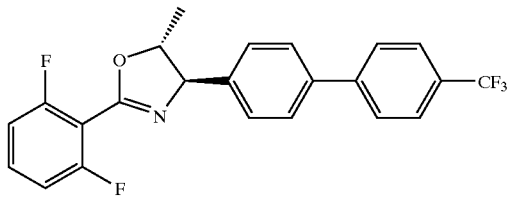

Isolated as a dark brown solid (35% yield): mp 120–121° C.; $^1$H NMR (CDCl$_3$) δ 7.68 (s, 4H), 7.64 (d, 1H), 7.38–7.48 (m, 3H), 7.30 (t, 2H), 4.98 (d, 1H), 4.67 (p, 1H), 1.62 (d, 3H); EI/MS 417 m/e (M$^+$).

Compound 27, (4R,5R)- and (4S,5S)-2-(2,6-difluorophenyl)-4-(4'-trifluoromethoxy-1,1'-biphenyl-4-yl)-5-methyl-4,5-dihydro-1,3-oxazole

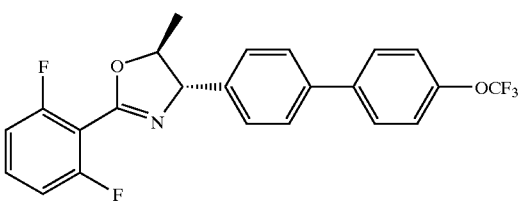

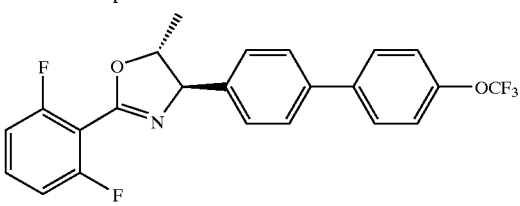

Isolated as a brown solid (62% yield): mp 101–102° C. $^1$H NMR (CDCl$_3$) δ 7.55–7.61 (m, 4H), 7.38–7.48 (m, 3H), 7.27 (d, 2H), 6.98 (t, 2H), 4.99 (d, 1H), 4.68 (m, 1H), 1.61 (d, 3H); EI/MS 433 m/e (M$^+$).

Compound 28, (4S,5S)- and (4R,5R)-2-(2,6-difluorophenyl)-5-methyl-4-[3'-(trifluoromethyl)-1,1'-biphenyl-4-yl]-4,5-dihydro-1,3-oxazole

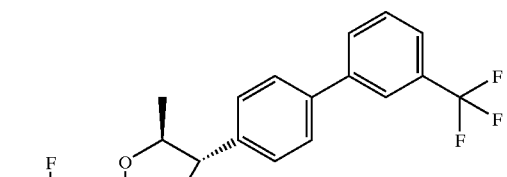

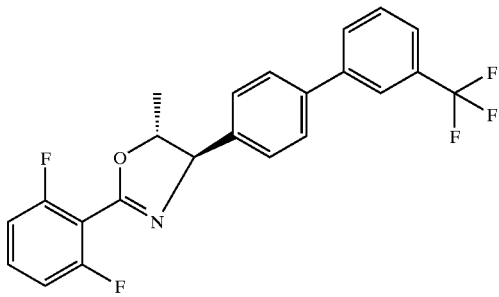

Isolated as a yellow oil (83% yield): $^1$H NMR (CDCl$_3$) δ 1.61 (d, 3H, J=6.2 Hz), 4.62–4.70 (m, 1H), 4.98 (d, 1H, J=7.3 Hz), 7.01 (t, 2H, J=8.42 Hz), 7.38–7.48 (m, 3 H), 7.52–7.62 (m, 4H), 7.76 (d, 1H, J=7.3 Hz), 7.82 (s, 1H); MS 418 m/e (M$^+$).

Compound 29, (4S,5S)- and (4R,5R)-2-(2,6-difluorophenyl)-4-(3',4'-dimethyl-1,1'-biphenyl-4-yl)-5-methyl-4,5-dihydro-1,3-oxazole

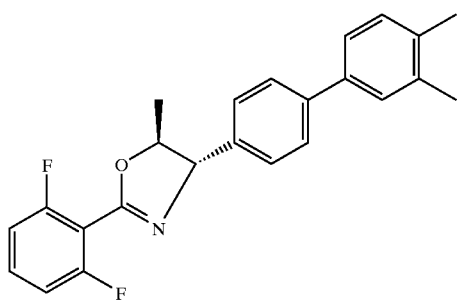

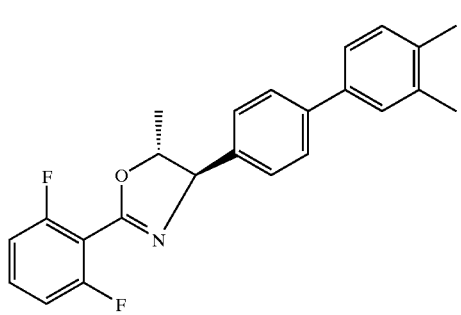

Isolated as a brown glass (72% yield): $^1$H NMR (CDCl$_3$) δ 1.61 (d, 3H, J=6.2 Hz), 2.32 (d, 6H, J=8.0 Hz), 4.64–4.73 (m, 1H), 4.97 (d, 1H, J=7.3 Hz), 6.97–7.05 (m, 2H), 7.21 (d, 1H, J=7.7 Hz), 7.32–7.48 (m, 5H), 7.60 (d, 2H, J=8.1 Hz); MS 378 m/e (M$^+$).

Compound 30, (4S,5S)- and (4R,5R)-2-(2,6-difluorophenyl)-4-(4'-isopropyl-1,1'-biphenyl-4-yl)-5-methyl-4,5-dihydro-1,3-oxazole

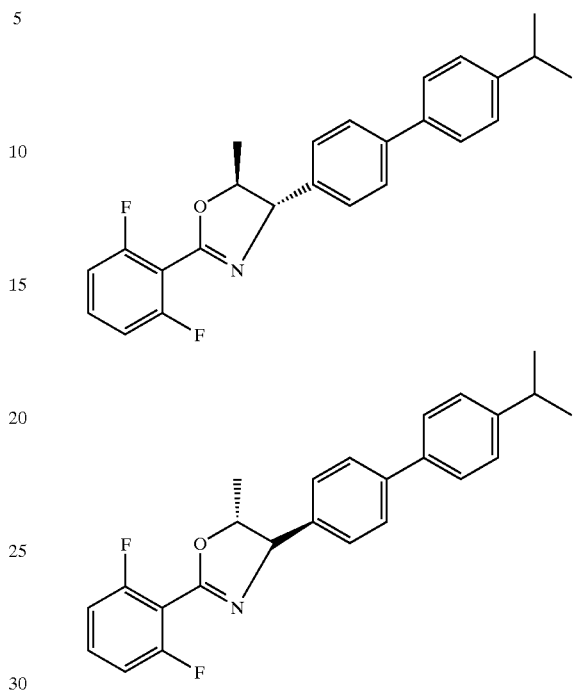

Isolated as a red oil (60% yield): $^1$H NMR (CDCl$_3$) δ 1.31 (d, 6H, J=6.6 Hz), 1.62 (d, 3H, J=6.2 Hz), 2.93–3.02 (m, 1H), 4.65–4.74 (m, 1H), 4.96 (d, 1H, J=7.3 Hz), 7.01 (t, 2H, J=8.42 Hz), 7.32 (d, 2H, J=8.0 Hz), 7.39–7.48 (m, 3H), 7.54 (d, 2H, J=7.7 Hz), 7.59 (d, 2H, J=7.7 Hz); MS 392 m/e (M$^+$).

Compound 31, (4S,5S)- and (4R,5R)-2-(2,6-difluorophenyl)-4-(2'-fluoro-1,1'-biphenyl-4-yl)-5-methyl-4,5-dihydro-1,3-oxazole

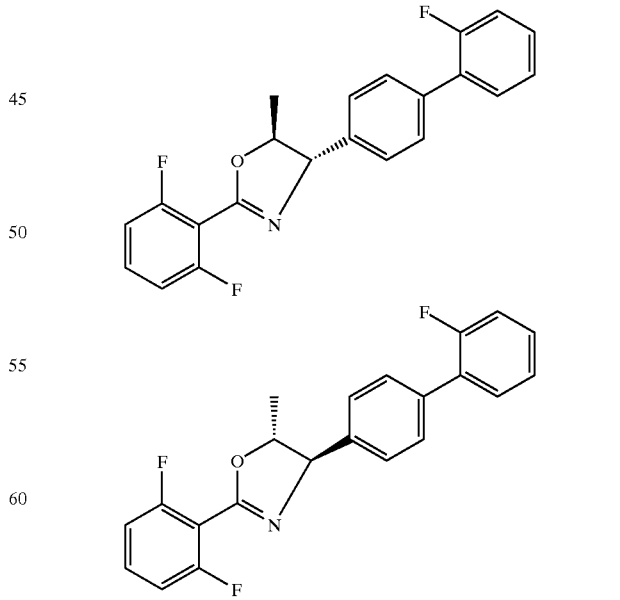

Isolated as a yellow oil (80% yield): $^1$H NMR (CDCl$_3$) δ 1.61 (d, 3H, J=6.2 Hz), 4.64–4.73 (m, 1H), 4.97 (d, 1H, J=7.0 Hz), 6.96–7.03 (m, 2H), 7.11–7.23 (m, 2H), 7.27–7.35 (m, 1H), 7.37–7.47 (m, 4H), 7.55–7.59 (m, 2H); MS 368 m/e (M⁺).

Compound 32, (4S,5S)- and (4R,5R)-2-(2,6-difluorophenyl)-4-[2'-fluoro-4'-(trifluoromethyl)-1,1'-biphenyl-4-yl]-5-methyl-4,5-dihydro-1,3-oxazole

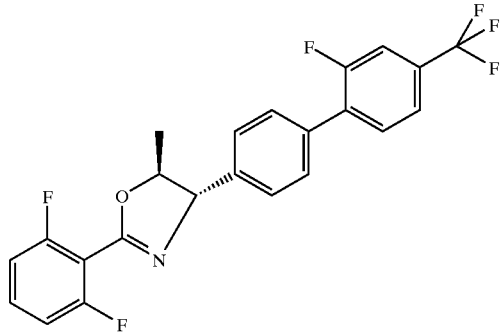

Isolated as orange crystals (50% yield): mp 97–101° C.; ¹H NMR (CDCl3) δ 1.62 (d, 3H, J=6.2 Hz), 4.64–4.72 (m, 1H), 4.99 (d, 1H, J=7.3 Hz), 7.01 (t, 2H, J=8.2 Hz), 7.38–7.50 (m, 5H), 7.56 (t, 3H, J=7.7; 7.3 Hz); MS 436 m/e (M⁺).

Compound 33, (4S,5S)- and (4R,5R)-2-(2,6-difluorophenyl)-4-(4'-ethoxy-1,1'-biphenyl-4-yl)-5-methyl-4,5-dihydro-1,3-oxazole

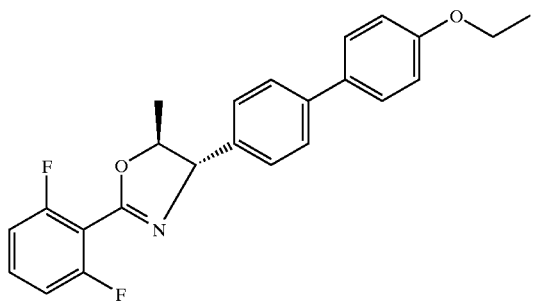

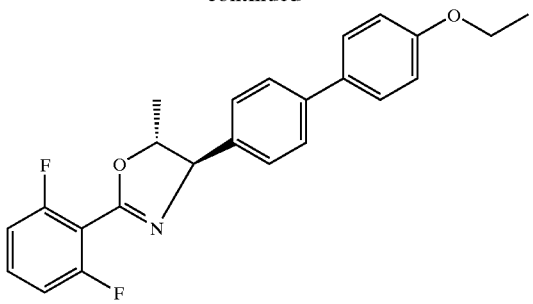

Isolated as a yellow solid (47% yield): mp 134–136° C.; ¹H NMR (CDCl₃) δ 1.45 (t, 3H, J=7.0 Hz), 1.60 (d, 3H, J=6.2 Hz), 4.04–4.11 (m, 2H), 4.63–4.71 (m, 1H), 4.96 (d, 1H, J=7.0 Hz), 6.92–7.04 (m, 4H), 7.36–7.45 (m, 3H), 7.47–7.58 (m, 4H); MS 394 m/e (M⁺).

Compound 34, (4S,5S)- and (4R,5R)-4-[4-(2,2-difluoro-1,3-benzodioxol-5-yl)phenyl]-2-(2,6-difluorophenyl)-5-methyl-4,5-dihydro-1,3-oxazole

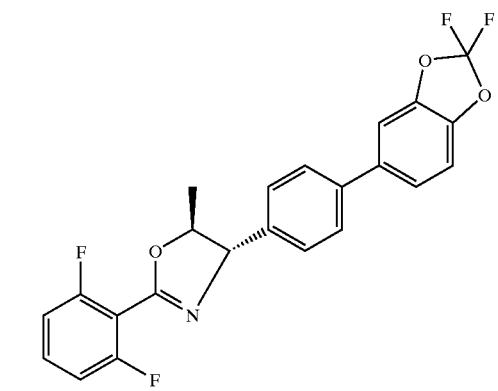

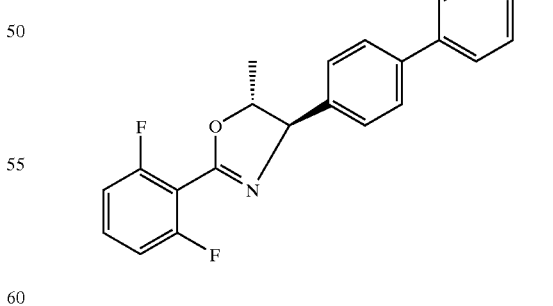

Isolated as yellow needles (34% yield): 129–133° C.; ¹H NMR (CDCl₃) δ 1.61 (d, 3H, J=6.2 Hz), 4.62–4.70 (m, 1H), 4.98 (d, 1H, J=7.3 Hz), 6.96–7.06 (m, 3H), 7.11–7.21 (m, 1H), 7.28 (s, 1H), 7.38–7.47 (m, 3H), 7.70 (d, 2H, J=8.1 Hz); MS 430 m/e (M⁺).

Compound 35, (4R,5R)- and (4S,5S)-4-phenyl-2-(2,6-difluorophenyl)-5-methyl-4,5-dihydro-1,3-oxazole

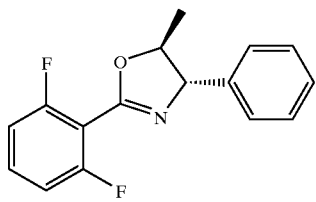

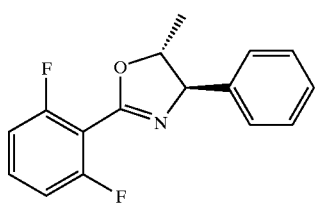

Isolated as a yellow oil (81% yield): $^1$H NMR (CDCl$_3$) δ 8.01–7.27 (m, 6H), 7.03–6.91 (m, 2H), 4.92 (d, J=6.96 Hz, 1H), 4.63 (dt, J=6.96, 6.22 Hz, 1H), 1.59 (d, J=6.22 Hz, 3H); EI/MS 231 m/e (M—CH$_3$CHO).

Compound 36, (4S,5S)- and (4R,5R)-2-(2,6-difluorophenyl)-5-methyl-4-(4'-methyl-1,1'-biphenyl-4-yl)-4,5-dihydro-1,3-oxazole

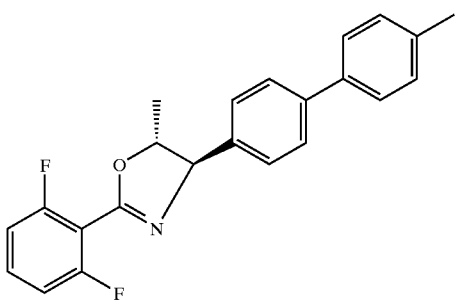

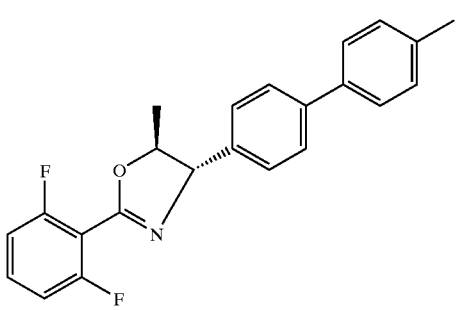

Isolated as a white solid (5% yield): mp 149–150° C.; $^1$H NMR (CDCl$_3$) δ 1.60 (d, 3H, J=6.2 Hz), 2.40 (s, 3H), 4.63–4.71 (m, 1H), 4.96 (d, 1H, J=7.3 Hz), 6.96–7.03 (m, 2H), 7.24 (d, 2H, J=7.0 Hz), 7.38 (d, 2H, J=8.1 Hz), 7.41–7.45 (m, 3H), 7.48 (d, 2H, J=8.1 Hz), 7.57–7.60 (m, 2H); MS 364 m/e (M$^+$).

Compound 37, (4S,5S)- and (4R,5R)-4-(4'-chloro-1,1'-biphenyl-4-yl)-2-(2,6-difluorophenyl)-5-methyl-4,5-dihydro-1,3-oxazole

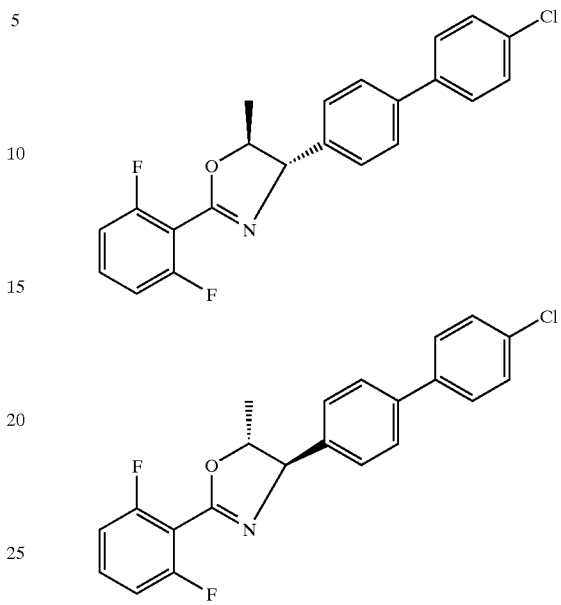

Isolated as brown crystals (18% yield): mp 160–161° C.; $^1$H NMR (CDCl$_3$) δ 1.61 (d, 3H, J=6.2 Hz), 4.62–4.70 (m, 1H), 4.97 (d, 1H, J=7.0 Hz), 7.01 (t, 2H, J=8.1, 8.4 Hz), 7.39–7.46 (m, 5H), 7.51 (d, 2H, J=8.8 Hz), 7.56 (d, 2H, J=8.4 Hz); MS 384 m/e (M$^+$).

Compound 38, (4R,5S)- and (4S,5R)-4-(4-bromo-2-methylphenyl)-2-(2,6-difluorophenyl)-5-methyl-4,5-dihydro-1,3-oxazole

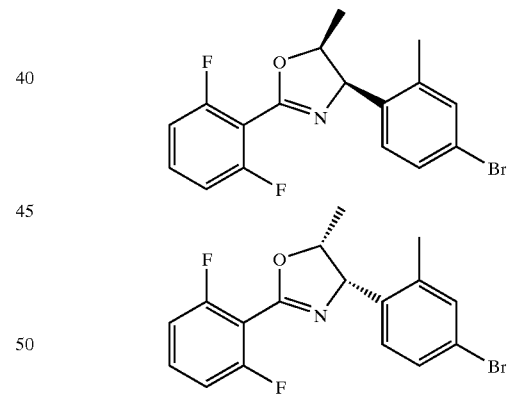

To a suspension of N-[(1R,2R)- and (1S,2S)-1-(4-bromo-2-methylphenyl)-2-hydroxypropyl]-2,6-difluorobenzamide (0.9 g, 2.2 mmol) in CH$_2$Cl$_2$ (25 mL) was added dropwise (diethylamino)sulfur trifluoride (0.36 g, 2.2 mmol) at −78° C. The cooling bath was removed and the yellow mixture was warmed to 25° C. The resulting light orange solution was stirred at 25° C. for 16 h. The reaction mixture was poured into 100 g of ice containing conc. NH$_4$OH (25 mL). The phases were separated and the aqueous layer was extracted with CH$_2$Cl$_2$ (2×50 mL). The organic extracts were combined, washed with brine, dried (Na$_2$SO$_4$), filtered, and concentrated in vacuo to give crude product as a brown oil. Flash chromatography (SiO$_2$; 0–20% Et$_2$O/Hexanes) afforded the racemic syn product (0.59 g, 73%) as a light yellow solid: mp 55–61° C.; ¹H NMR (CDCl₃) δ 0.88 (d, 3H, J=6.6 Hz), 2.29 (s, 3H), 5.21–5.29 (m, 1H), 5.64 (d, 1H, J=9.9 Hz), 7.00 (t, 2H, J=8.0 Hz), 7.30–7.48 (m, 4H); EI/MS 366 m/e (M⁺).

Compound 39, (4R,5S)- and (4S,5R)-2-(2,6-difluorophenyl)-5-methyl-4-[3-methyl-4'-(trifluoromethyl)-1,1'-biphenyl-4-yl]-4,5-dihydro-1,3-oxazole

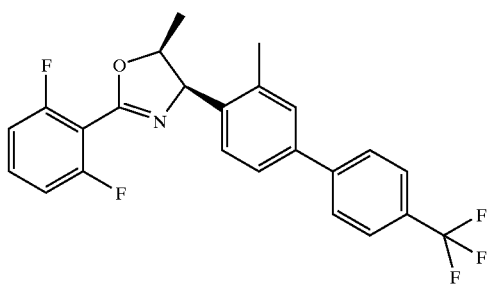

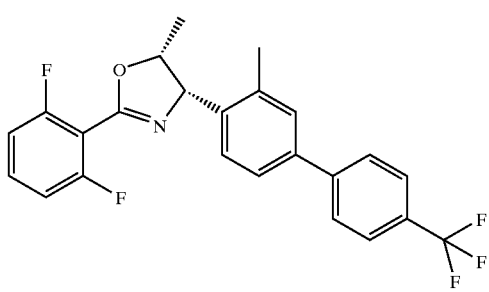

Suzuki coupling parallel synthesis approach to obtain the desired targets is as described for Compound 39.

To the reaction vessel were added (4R,5S)- and (4S,5R)-4-(4-bromo-2-methylphenyl)-2-(2,6-difluorophenyl)-5-methyl-4,5-dihydro-1,3-oxazole (0.18 g, 0.5 mmol), Na₂CO₃ (0.08 g, 0.7 mmol), dichlorobis(triphenylphosphine) palladium(II) (0.02 g, 0.03 mmol), tri-o-tolylphosphine (0.02 g, 0.05 mmol), and 4-(trifluoromethyl)benzeneboronic acid (0.12 g, 0.63 mmol). To the solid reagents was added a 10% solution of water in CH₃CN with mechanical agitation. The reaction was heated to 70° C., and the resulting amber mixture was mechanically agitated for 16 h. The reaction was cooled to 25° C. and filtered. The solids were removed by filtration and washed with additional CH₃CN/H₂O. The solvents were removed in vacuo, and the residue was dissolved in CH₂Cl₂. The solids were removed by filtration and the CH₂Cl₂ removed in vacuo. Preparative liquid chromatography afforded a waxy yellow solid (0.10 g, 52%): mp 113–116° C.; ¹H NMR (CDCl₃) δ 0.95 (d, 3H, J=6.6 Hz), 2.40 (s, 3H), 5.25–5.32 (m, 1H), 5.76 (d, 1H, J=9.9 Hz), 7.02 (t, 2H, J=8.0 Hz), 7.40–7.50 (m, 3H), 7.55 (d, 1H, J=8.0 Hz), 7.66–7.73 (m, 4H); EI/MS 432 m/e (M⁺).

Compound 40, (4R,5S)- and (4S,5R)-2-(2,6-difluorophenyl)-5-methyl-4-[3-methyl-4'-(trifluoromethoxy)-1,1'-biphenyl-4-yl]-4,5-dihydro-1,3-oxazole

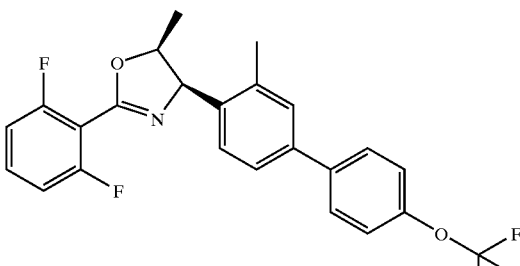

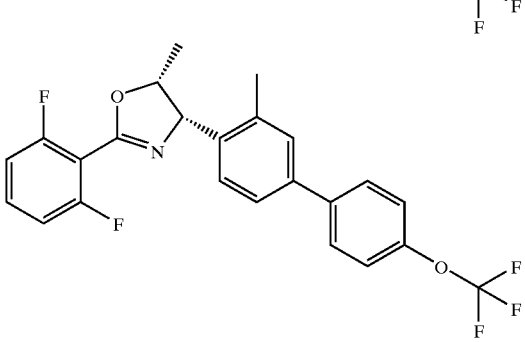

Isolated as an orange oil (72% yield): ¹H NMR (CDCl₃) δ 0.94 (d, 3H, J=6.6 Hz), 2.39 (s, 3H), 5.26–5.32 (m, 1H), 5.75 (d, 1H, J=9.9 Hz), 7.02 (t, 2H, J=8.2 Hz), 7.26–7.63 (m, 8H); EI/MS 448 m/e (M⁺).

Compound 41, (4R,5S)- and (4S,5R)-2-(2,6-difluorophenyl)-4-(4'-ethoxy-3-methyl-1,1'-biphenyl-4-yl)-5-methyl-4,5-dihydro-1,3-oxazole

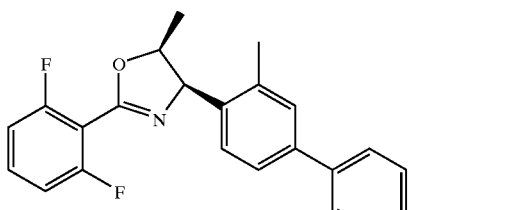

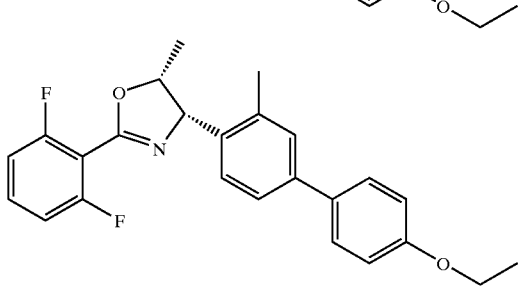

Isolated as a yellow solid (44% yield): mp 74–76° C.; ¹H NMR (CDCl₃) δ 0.94 (d, 3H, J=6.6 Hz), 1.44 (t, 3H, J=7.0 Hz), 2.37 (s, 3H), 4.08 (q, 2H, J=7.0 Hz), 5.25–5.32 (m, 1H), 5.74 (d, 1H, J=9.9 Hz), 6.96 (dd, 2H, J=2.0, 6.8 Hz), 7.02 (t, 2H, J=8.2 Hz), 7.37–7.51 (m, 4H), 7.54 (dd, 2H, J=2.2, 6.6 Hz); EI/MS 408 m/e (M⁺).

Compound 42, (4S,5S)- and (4R,5R)-4-(4-bromo-2-methylphenyl)-2-(2,6-difluorophenyl)-5-methyl-4,5dihydro-1,3-oxazole

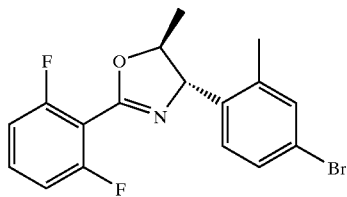

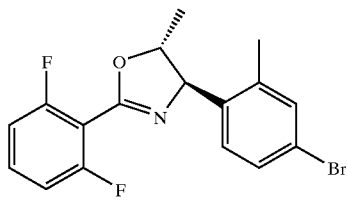

N-[(1R,2S)- and (1S,2R)-1-(4-Bromo-2-methylphenyl)-2-hydroxypropyl]-2,6-difluorobenzamide were subjected to the same reaction, work-up, and purification conditions as described for Compound 38 to give the racemic anti product as a peach solid (90% yield): mp 38–45° C.; $^1$H NMR (CDCl$_3$) δ 1.59 (d, 3H, J=6.2 Hz), 2.38 (s, 3H), 4.57 (dq, 1H, J=6.2, 6.2 Hz), 5.13 (d, 1H, J=6.2 Hz), 7.00 (t, 2H, J=8.0 Hz), 7.17 (d, 1H, J=8.4 Hz), 7.34–7.48 (m, 3H); EI/MS 366 m/e (M$^+$).

Compound 43, (4S,5S)- and (4R,5R)-2-(2,6-difluorophenyl)-5-methyl-4-[3-methyl-4'-(trifluoromethyl)-1,1'-biphenyl-4-yl]-4,5-dihydro-1,3-oxazole

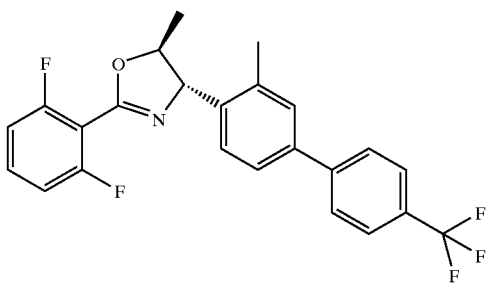

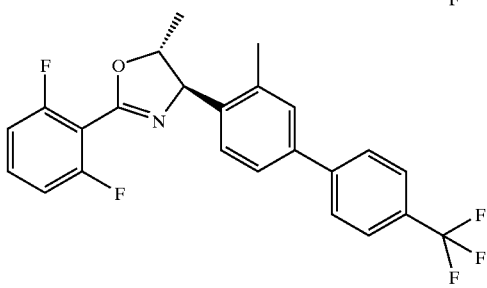

(4S,5S)- and (4R,5R)-4-(4-Bromo-2-methylphenyl)-2-(2,6-difluorophenyl)-5-methyl-4,5-dihydro-1,3-oxazole were subjected to the same parallel synthesis conditions described above for Compound 39. Isolated as a yellow solid (59% yield): mp 77–79° C.; $^1$H NMR (CDCl$_3$) δ 1.64 (d, 3H, J=6.2 Hz), 2.50 (s, 3H), 4.67 (dq, 1H, J=5.9, 6.2 Hz), 5.24 (d, 1H, J=5.9 Hz), 7.02 (t, 2H, J=8.0 Hz), 7.40–7.50 (m,4H), 7.68 s, 4H); EI/MS 432 m/e (M$^+$).

Compound 44, (4S,5S)- and (4R,5R)-2-(2,6-difluorophenyl)-5-methyl-4-[3-methyl-4'-(trifluoromethoxy)-1,1'-biphenyl-4-yl]-4,5-dihydro-1,3-oxazole

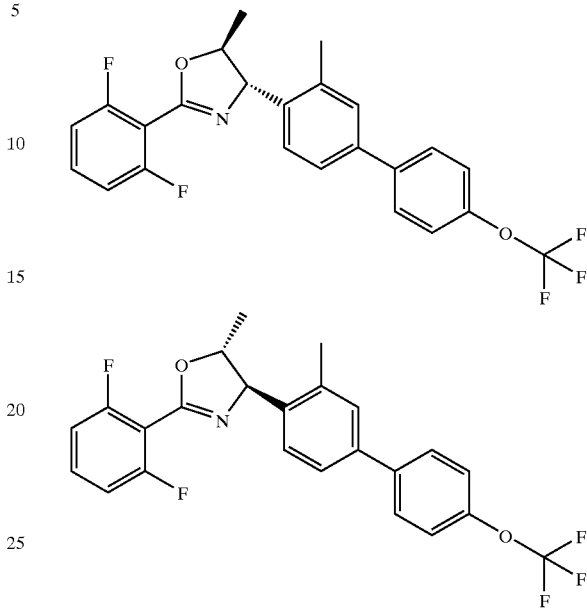

Isolated as an orange oil (77% yield): $^1$H NMR (CDCl$_3$) δ 1.63 (d, 3H, J=6.2 Hz), 2.48 (s, 3H), 4.66 (dq, 1H, J=6.2, 6.2 Hz), 5.23 (d, 1H, J=6.2 Hz), 7.02 (t, 2H, J=8.4 Hz ), 7.26–7.29 (m, 2H), 7.37–7.47 (m, 4H), 7.59 (dd, 2H, J=2.2, 6.6 Hz); EI/MS 448 m/e (M$^+$).

Compound 45, (4S,5S)- and (4R,5R)-2-(2,6-difluorophenyl)-4-(4'-ethoxy-3-methyl-1,1'-biphenyl-4-yl)-5-methyl-4,5-dihydro-1,3-oxazole

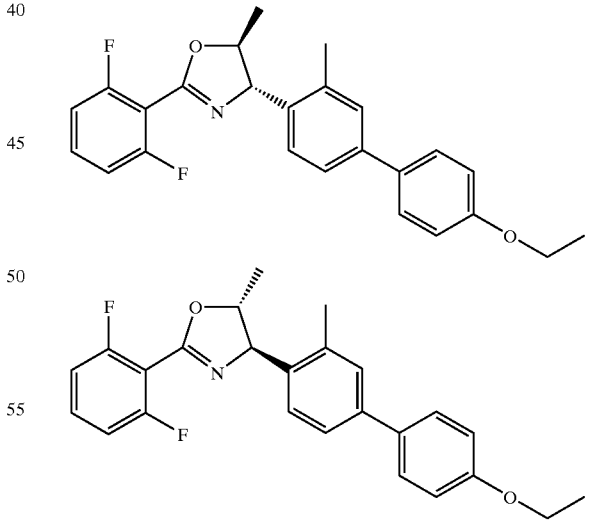

Isolated as an orange solid (16% yield): mp 112–114° C.; $^1$H NMR (CDCl$_3$) δ 1.44 (t, 3H, J=7.0 Hz), 1.62 (d, 3H, J=6.2 Hz), 2.47 (s, 3H), 4.08 (q, 2H, J=7.0 Hz), 4.66 (dq, 1H, J=6.2, 6.2 Hz), 5.22 (d, 1H, J=6.2 Hz), 6.96 (dd, 2H, J=2.2, 6.6 Hz), 7.01 (t, 2H, J=8.0 Hz), 7.33–7.46 (m, 4H), 7.54 (dd, 2H, J=2.2, 7.0 Hz); EI/MS 408 m/e (M$^+$).

Compound 46, (4S,5S)-4-(4-bromophenyl)-2-(2,6-difluorophenyl)-5-methyl-4,5 dihydro-1,3-oxazole

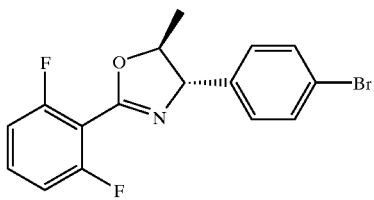

and

Compound 48, (4S,5R)-4-(4-bromophenyl)-2-(2,6-difluorophenyl)-5-methyl-4,5-dihydro-1,3-oxazole

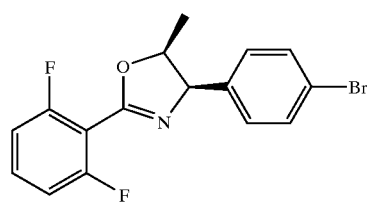

A 50 mL round bottom flask equipped with a stir bar, thermocouple, and a reflux condenser was charged with (2R)-1-amino-1-(4-bromophenyl)propan-2-ol (480 mg, 2.09 mmol), triethylamine (222 mg, 0.3 mL, 2.19 mmol) and THF (10 mL). The reaction mixture was cooled to 10° C. 2,6-Difluorobenzoyl chloride (387 mg, 2.1 mmol) was added to the THF solution keeping the temperature <30° C. The reaction mixture was stirred at 25–30° C. for 2 hours. Dichloromethane (40 mL) and water (60 mL)were added and the phases were separated. The aqueous layer was extracted with dichloromethane (2×20 mL). The combined organic extracts were washed with aq. 0.5 N HCl (50 mL) and brine (50 mL), dried over sodium sulfate, filtered, and concentrated under reduced pressure to give crude amide, which was placed in a 50 mL round bottom flask equipped with a stir bar, thermocouple, and a reflux condenser. The residue was dissolved in dichloromethane (25 mL), and the reaction mixture was cooled to −78° C. (Diethylamino)sulfur trifluoride (337 mg, 0.28 mL, 2.09 mmol) was added to the dichloromethane solution keeping the temperature −70° C. The reaction mixture was allowed to warm to 25° C. while stirring over 16 h. The reaction mixture was poured into 50 g ice containing conc. ammonium hydroxide (5 mL). The phases were separated and the aqueous layer was extracted with dichloromethane (2×50 mL). The combined organic extracts were washed with brine (50 mL), dried over sodium sulfate, filtered, and concentrated under reduced pressure to give crude product as a mixture of diastereomers. Column chromatography gave two products (270 mg of (4S,5S) as an oil and 171 mg of (4S,5R) as an oil, 60% overall yield for the combined isomers over the two steps).
Compound 46: $^1$H NMR (CDCl$_3$) δ 7.50 (d, 2H, J=8.4 Hz), 7.43 (m, 1H), 7.20 (d, 2H, J=8.4 Hz), 7.00 (tm, 2H, J=8.4 Hz), 4.88 (d, 1H, J=7.3 Hz), 3.99 (dq, 1H, J=7.3, 6.2 Hz), 1.58 (d, 3H, J=6.2 Hz); EI/MS 352 m/e (M$^+$).

Compound 48: $^1$H NMR (CDCl$_3$) δ 7.50 (d, 2H, J=8.4 Hz), 7.43 (m, 1H), 7.16 (d, 2H, J=8.1 Hz), 7.03 (tm, 2H, J=8.4 Hz), 5.48 (d, 1H, J=9.9 Hz), 5.15 (m, 1H), 0.98 (d, 3H, J=6.6 Hz); EI/MS 352 m/e (M$^+$).

Compound 47, (4S,5S)-2-(2,6-difluorophenyl)-5-methyl-4-[4'-(trifluoromethoxy)-1,1'-biphenyl-4-yl]-4,5-dihydro-1,3-oxazole

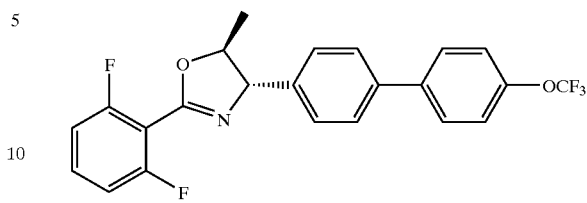

A 20 mL round bottom flask equipped with a magnetic stirrer, reflux condenser, nitrogen inlet and thermocouple was charged with (4S,5S)-4-(4-bromophenyl)-2-(2,6-difluorophenyl)-5-methyl-4,5-dihydro-1,3-oxazole (217 mg, 0.616 mmol), 4-(trifluoromethoxy)benzene boronic acid (152 mg, 0.739 mmol), sodium carbonate (130 mg, 1.232 mmol), tetrakis(triphenylphosphine)palladium(O) (36 mg, 0.031 mmol) and ethyl alcohol (6 mL). The mixture was heated to 78° C. for 7 hours and then cooled to 25° C. and stirred for 16 hours. 1N aq HCl (1 mL) and water (10 mL) were added, and the mixture was extracted with diethyl ether (2×20 mL). The combined organic extracts were dried over sodium sulfate and concentrated under reduced pressure. Column chromatography (4:1 hexane:diethyl ether) afforded the product (231 mg, 87%) as a pale yellow solid: mp 87–91° C.; $^1$H NMR (CDCl$_3$) δ 7.58 (dd, 4H, J=8.4, 5.9 Hz), 7.48–7.40 (m, 3H), 7.28 (d, 2H, J=8.0 Hz), 7.02 (t, 2H, J=8.4 Hz), 4.99 (d, 1H, J=7.0 Hz), 4.70 (dq, 1H, J=7.0, 6.3 Hz), 1.63 (d, 3H, J=6.3 Hz); EI/MS 433 m/e (M$^+$); Chiracel OJ HPLC column shows 94% ee; [α]$_D$=−54.1° (c 1.00, CHCl$_3$); Anal. Calcd. for C$_{23}$H$_{16}$F$_2$NO$_2$: C, 63.74; H, 3.72; N, 3.23. Found: C, 63.49; H, 3.81; N, 3.20.

Compound 49, (4S,5R)-2-(2,6-difluorophenyl)-5-methyl-4-[4'-(trifluoromethoxy)-1,1'-biphenyl-4-yl]-4,5-dihydro-1,3-oxazole

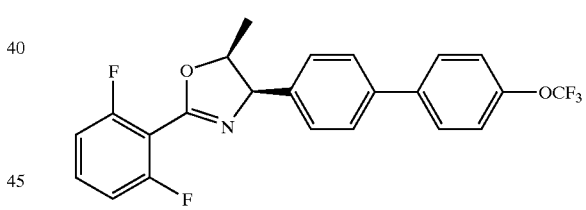

A 20 mL round bottom flask equipped with a magnetic stirrer, reflux condenser, nitrogen inlet and thermocouple was charged with (4S,5R)-4-(4-bromophenyl)-2-(2,6-difluorophenyl)-5-methyl-4,5-dihydro-1,3-oxazole (171 mg, 0.486 mmol), 4-(trifluoromethoxy)benzene boronic acid (120 mg, 0.583 mmol), sodium carbonate (103 mg, 0.972 mmol), tetrakis(triphenylphosphine)palladium(O) (28 mg, 0.024 mmol) and ethyl alcohol (5 mL). The reaction mixture was heated to 78° C. for 7 hours and then cooled to 25° C. and stirred for 16 hours. 1N aq HCl (1 mL) and water (10 mL) were added and the aqueous layer was extracted with diethyl ether (2×20 mL). The combined organic extracts were dried over sodium sulfate and concentrated under reduced pressure. Column chromatography (4:1 hexane:diethyl ether) afforded the product (131 mg, 62%) as a pale yellow solid: mp 80–83° C.; $^1$H NMR (CDCl$_3$) δ 7.63–7.54 (m, 4H), 7.48–7.38 (m, 1H), 7.35 (d, 2H, J=8.4 Hz), 7.28 (d, 2H, J=8.4 Hz), 7.01 (t, 2H, J=8.1 Hz), 5.55 (d, 1H, J=9.9 Hz), 5.18 (m, 1H), 1.03 (d, 3H, J=6.6 Hz); EI/MS 433 m/e (M$^+$); Chiracel OJ HPLC column shows 96% ee; [α]$_D$=+

1.3° (c 1.00, CHCl₃); Anal. Calcd. for $C_{23}H_{16}F_2NO_2$: C, 63.74; H, 3.72; N, 3.23. Found: C, 63.88; H, 3.94; N, 3.21.
Compound 50, (4R,5S)-4-(4-bromophenyl)-2-(2,6-difluorophenyl)-5-methyl-4,5-dihydro-1,3-oxazole

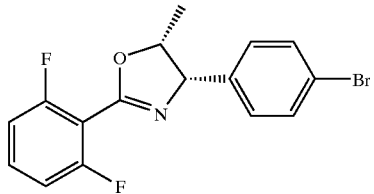

and
Compound 52, (4R,5R)-4-(4-bromophenyl)-2-(2,6-difluorophenyl)-5-methyl-4,5-dihydro-1,3-oxazole

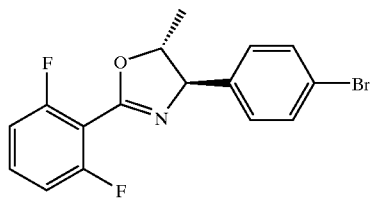

A 50 mL round bottom flask equipped with a magnetic stirrer, rubber septum, thermocouple, and a reflux condenser was charged with NaBH₄ (253 mg, 6.68 mmol) and THF (15 mL). Trifluoroacetic acid (762 mg, 0.52 mL, 6.68 mmol) was slowly added to the NaBH₄ suspension via syringe through the rubber septum. Gas evolution occurred and the temperature increased to 27° C. from 23° C. A solution of (1S,2E/Z)-2-(4-bromophenyl)-2-(methoxyimino)-1-methylethyl acetate (500 mg, 1.67 mmol) in THF (5 mL) was slowly added to the reaction mixture. The reaction mixture was heated to 60° C. for 8 hours and then cooled to 25° C. The pH was adjusted to <3 by the careful addition of conc. HCl to neutralize the remaining NaBH₄. The pH was adjusted to >9 with 50% aq. NaOH. Water (50 mL) and dichloromethane (50 mL) were added and the phases were separated. The aqueous layer was extracted with dichloromethane (3×20 mL). The combined organic extracts were washed with brine (20 mL), dried over sodium sulfate, filtered, and concentrated under reduced pressure to give crude amino alcohol, (2S)-1-amino-1-(4-bromophenyl)propan-2-ol, (382 mg) as a waxy low-melting solid. A 50 mL round bottom flask equipped with a stir bar, thermocouple, and a reflux condenser was charged with the crude (2S)-1-amino-1-(4-bromophenyl)propan-2-ol from above (382 mg, 1.66 mmol), triethylamine (171 mg, 0.23 mL, 1.69 mmol) and THF (10 mL). The reaction mixture was cooled to 10° C. 2,6-Difluorobenzoyl chloride (295 mg, 1.67 mmol) was added to the THF solution keeping the temperature <30° C. The reaction mixture was stirred at 25–30° C. for 2 hours. Dichloromethane (40 mL) and water (60 mL) were added and the phases were separated. The aqueous layer was extracted with dichloromethane (2×20 mL). The combined organic extracts were washed with aq. 0.5 N HCl (50 mL) and brine (50 mL), dried over sodium sulfate, filtered, and concentrated under reduced pressure. The crude amide intermediate was placed in a 50 mL round bottom flask equipped with a stir bar, thermocouple, and a reflux condenser and was charged with dichloromethane (25 mL). The reaction mixture was cooled to −78° C. (Diethylamino)sulfur trifluoride (269 mg, 0.22 mL, 1.67 mmol) was added to the dichloromethane solution keeping the temperature <−70° C. The reaction mixtured was allowed to warm to 25° C. while stirring over 16 hours. The reaction mixture was poured into 50 g ice containing conc. ammonium hydroxide (5 mL). The phases were separated, and the aqueous layer was extracted with dichloromethane (2×50 mL). The combined organic extracts were washed with brine (50 mL), dried over sodium sulfate, filtered, and concentrated under reduced pressure to give crude product as a mixture of diastereomers. Column chromatography gave two products (100 mg of (4R,5R) as an oil and 100 mg of (4R,5S) as an oil, 34% overall yield for the combined isomers over the three steps).

Compound 52, (4R,5R)-4-(4-bromophenyl)-2-(2,6-difluorophenyl)-5-methyl-4,5-dihydro-1,3-oxazole: ¹H NMR (CDCl₃) δ 7.50 (d, 2H, J=8.4 Hz), 7.43 (m, 1H), 7.20 (d, 2H, J=8.4 Hz), 7.00 (tm, 2H, J=8.4 Hz), 4.88 (d, 1H, J=7.3 Hz), 3.99 (dq, 1H, J=7.3, 6.2 Hz), 1.58 (d, 3H, J=6.2 Hz).

Compound 50, (4R, 5S)-4-(4-bromophenyl)-2-(2,6-difluorophenyl)-5-methyl-4,5-dihydro-1,3-oxazole: ¹H NMR (CDCl₃) δ 7.50 (d, 2H, J=8.4 Hz), 7.43 (m, 1H), 7.16 (d, 2H, J=8.1 Hz), 7.03 (tm, 2H, J=8.4 Hz), 5.48 (d, 1H, J=9.9 Hz), 5.15 (m, 1H), 0.98 (d, 3H, J=6.6 Hz).

Compound 51, (4R,5S)-2-(2,6-difluorophenyl)-5-methyl-4-[4'-(trifluoromethoxy)-1,1'-biphenyl-4-yl]-4,5-dihydro-1,3-oxazole

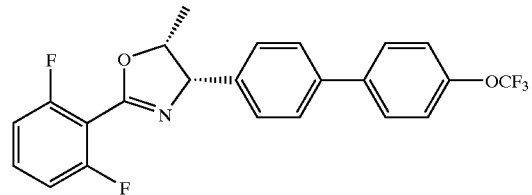

A 20 mL round bottom flask equipped with a magnetic stirrer, reflux condenser with nitrogen inlet and thermocouple was charged with (4R,5S)-4-(4-bromophenyl)-2-(2,6-difluorophenyl)-5-methyl-4,5-dihydro-1,3-oxazole (100 mg, 0.284 mmol), 4-(trifluoromethoxy)benzeneboronic acid (70 mg, 0.341 mmol), sodium carbonate (60 mg, 0.566 mmol), tetrakis(triphenylphosphine)palladium(0) (20 mg, 0.017 mmol) and ethyl alcohol (4 mL). The reaction mixture was heated to 78° C. for 7 hours and then cooled to 25° C. and stirred for 16 hours. 1N aq HCl (1 mL) and water (10 mL) were added, and the aqueous layer was extracted with diethyl ether (2×20 mL). The combined organic extracts were dried over sodium sulfate and concentrated under reduced pressure. Column chromatography (4:1 hexane:diethyl ether) afforded the product (38 mg, 31% yield) as a gummy solid: ¹H NMR (CDCl₃) δ 7.63–7.54 (m, 4H), 7.48–7.38 (m, 1H), 7.35 (d, 2H, J=8.4 Hz), 7.28 (d, 2H, J=8.4 Hz), 7.01 (t, 2H, J=8.1 Hz), 5.55 (d, 1H, J=9.9 Hz), 5.18 (m, 1H), 1.03 (d, 3H, J=6.6 Hz); EI/MS 433 m/e (M⁺); Chiracel OJ HPLC column shows 74% ee.

Compound 53, (4R,5R)-2-(2,6-difluorophenyl)-5-methyl-4-[4'-(trifluoromethoxy)-1,1'-biphenyl-4-yl]-4,5-dihydro-1,3-oxazole

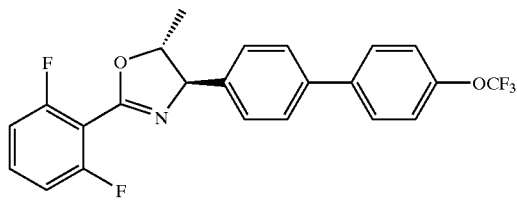

A 20 mL round bottom flask equipped with a magnetic stirrer, reflux condenser, nitrogen inlet and thermocouple was charged with (4R,5R)-4-(4-bromophenyl)-2-(2,6-difluorophenyl)-5-methyl-4,5-dihydro-1,3-oxazole (100 mg, 0.284 mmol), 4-(trifluoromethoxy)benzeneboronic acid (70 mg, 0.341 mmol), sodium carbonate (60 mg, 0.566 mmol), tetrakis(triphenylphosphine)palladium(O) (20 mg, 0.017 mmol) and ethyl alcohol (4 mL). The reaction mixture was heated to 78° C. for 6 hours and then cooled to 25° C. and stirred for 16 hours. 1N aq HCl (1 mL) and water (10 mL) were added, and the aqueous layer was extracted with diethyl ether (2×20 mL). The combined organic extracts were dried over sodium sulfate and concentrated under reduced pressure. Column chromatography (4:1 hexane:diethyl ether) afforded the product (65 mg contains phosphine impurity) as a yellow solid. Recrystallization from hexane/diethyl ether gave the product (30 mg, 24% yield) as a yellow solid: mp 81–83° C.; $^1$H NMR (CDCl$_3$) δ 7.58 (dd, 4H, J=8.4, 5.9 Hz), 7.48–7.40 (m, 3H), 7.28 (d, 2H, J=8.0 Hz), 7.02 (t, 2H, J=8.4 Hz), 4.99 (d, 1H, J=7.0 Hz), 4.70 (dq, 1H, J=7.0, 6.3 Hz), 1.63 (d, 3H, J=6.3 Hz); EI/MS 433 m/e (M$^+$); Chiracel OJ HPLC column shows 93% ee.

Phytologically acceptable acid addition salts of the compounds of formula (I) are also within the scope of the invention. For example, boron tetrafluoride, hydrogen chloride, hydrogen bromide, hydrogen iodide, hydrogen sulfate, or organic acid salts may be used.

The compounds identified in the following Tables were prepared using the procedures illustrated in the foregoing examples, and the compounds were tested against tobacco budworm, beet armyworm, cabbage looper, cotton aphid, two-spotted spider mite and sweetpotato whitefly using procedures described hereinafter.

TABLE 1

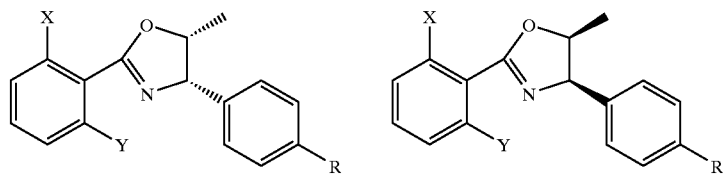

| Compd number | X, Y | R | mp ° C. | TBW | BAW | CL | CA | SM | WF |
|---|---|---|---|---|---|---|---|---|---|
| 1 | F, F | —I | Gum | F | F | D | A | A | D |
| 2 | F, F | —Br | 65–67 | G | F | F | A | A | A |
| 3 | F, Cl | —Br | Gum | G | G | A | B | A | A |
| 4 | F, Cl | —C$_6$H$_4$-CF$_3$ | 118–119 | A | A | A | A | A | G |
| 5 | F, F | —C$_6$H$_4$-CF$_3$ | 105–106 | B | A | A | B | A | G |
| 6 | F, F | —C$_6$H$_4$-OCF$_3$ | 106–109 | A | A | A | A | A | B |
| 7 | F, F | —C$_6$H$_4$-i-Pr | oil | A | A | A | — | D | A |
| 8 | F, F | —C$_6$H$_3$(Me)-Me | 101–111 | D | A | A | — | — | — |

TABLE 1-continued
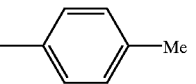
| Compd number | X, Y | R | mp °C. | TBW | BAW | CL | CA | SM | WF |
|---|---|---|---|---|---|---|---|---|---|
| 9 | F, F | –C₆H₄–Me (4-) | 149–152 | F | A | A | — | — | — |
| 10 | F, F | –C₆H₄–Cl (4-) | 147–148 | A | A | A | — | — | — |
| 11 | F, F | –C₆H₄–CF₃ (3-) | glass | B | A | A | — | — | — |
| 12 | F, F | –C₆H₄–OEt (4-) | 128–130 | B | A | A | — | — | — |
| 13 | F, F | benzodioxole-CF₂ | 132–134 | F | G | A | — | — | — |
| 14 | F, F | –C₆H₄–F (4-) | 140–142 | — | — | — | — | — | — |
| 15 | F, F | –C₆H₄–F (2-) | oil | A | A | A | — | — | — |
| 16 | F, F | –C₆H₃(2-F)(4-CF₃) | 111–112 | A | A | A | — | — | — |
| 17 | H, CH₃ | —Br | oil | F | G | F | — | — | — |
| 18 | H, CH₃ | –C₆H₄–OCF₃ | oil | — | — | — | — | — | — |
| 19 | H, CH₃ | –C₆H₄–CF₃ | oil | — | — | — | — | — | — |
| 20 | F, Cl | –C₆H₄–OCF₃ | 100–102 | — | — | — | — | — | — |

TABLE 1-continued

| Compd number | X, Y | R | mp °C. | TBW | BAW | CL | CA | SM | WF |
|---|---|---|---|---|---|---|---|---|---|
| 21 | F, Cl | —⟨⟩—OEt | oil | — | — | — | — | — | — |

TABLE 2

| Compd number | X, Y | R | mp °C. | TBW | BAW | CL | CA | SM | WF |
|---|---|---|---|---|---|---|---|---|---|
| 22 | F, F | —I | oil | G | A | F | A | A | — |
| 23 | F, Cl | —Br | 90–93 | B | G | F | — | A | G |
| 24 | F, F | —Br | 85–87 | F | G | F | A | A | G |
| 25 | F, F | —⟨⟩—F | 126–128 | A | A | A | — | A | G |
| 26 | F, F | —⟨⟩—CF₃ | 120–121 | A | A | A | G | A | G |
| 27 | F, F | —⟨⟩—OCF₃ | 101–102 | B | A | A | E | A | G |
| 28 | F, F | —⟨⟩-m-CF₃ | oil | A | A | A | — | A | G |
| 29 | F, F | —⟨⟩(Me)(Me) | glass | F | D | A | — | G | G |
| 30 | F, F | —⟨⟩—i-Pr | oil | A | A | A | — | C | F |

TABLE 2-continued

| Compd number | X, Y | R | mp ° C. | TBW | BAW | CL | CA | SM | WF |
|---|---|---|---|---|---|---|---|---|---|
| 31 | F, F | 2-F-phenyl | oil | F | F | A | — | A | G |
| 32 | F, F | 3-F-4-CF₃-phenyl | 97–101 | A | A | A | — | C | F |
| 33 | F, F | 4-OEt-phenyl | 134–136 | B | A | A | — | B | G |
| 34 | F, F | 2,2-difluoro-benzodioxole | 129–133 | F | G | A | — | — | — |
| 35 | F, F | H | oil | F | G | F | — | — | — |
| 36 | F, F | 4-Me-phenyl | 149–150 | F | F | A | — | — | — |
| 37 | F, F | 4-Cl-phenyl | 160–161 | A | A | A | — | — | — |

TABLE 3

| Compd number | X, Y | R | mp ° C. | TBW | BAW | CL | CA | SM | WF |
|---|---|---|---|---|---|---|---|---|---|
| 38 | F, F | —Br | 55–61 | G | G | G | — | D | F |
| 39 | F, F | 4-CF₃-phenyl | 113–116 | A | A | A | — | B | F |

TABLE 3-continued

| Compd number | X, Y | R | mp °C. | TBW | BAW | CL | CA | SM | WF |
|---|---|---|---|---|---|---|---|---|---|
| 40 | F, F | ―⌬―OCF₃ | oil | A | A | A | ― | B | F |
| 41 | F, F | ―⌬―OEt | 74–76 | A | A | A | ― | D | G |

TABLE 4

| Compd number | X, Y | R | mp °C. | TBW | BAW | CL | CA | SM | WF |
|---|---|---|---|---|---|---|---|---|---|
| 42 | F, F | —Br | 38–45 | F | G | G | — | G | G |
| 43 | F, F | ―⌬―CF₃ | 77–79 | A | A | A | — | G | F |
| 44 | F, F | ―⌬―OCF₃ | oil | A | A | A | — | C | G |
| 45 | F, F | ―⌬―OEt | 112–114 | A | A | A | — | F | — |

TABLE 5

| Compd number | X, Y | R | mp °C. | TBW | BAW | CL | CA | SM | WF |
|---|---|---|---|---|---|---|---|---|---|
| 46 | F, F | —Br | oil | G | G | G | A | A | G |

TABLE 5-continued

| Compd number | X, Y | R | mp °C. | TBW | BAW | CL | CA | SM | WF |
|---|---|---|---|---|---|---|---|---|---|
| 47 | F, F | —⌬—OCF₃ | 87–91 | F | A | A | B | A | F |

TABLE 6

| Compd number | X, Y | R | mp °C. | TBW | BAW | CL | CA | SM | WF |
|---|---|---|---|---|---|---|---|---|---|
| 48 | F, F | —Br | oil | — | — | — | — | — | — |
| 49 | F, F | —⌬—OCF₃ | 80–83 | B | A | A | B | A | B |

TABLE 7

| Compd number | X, Y | R | mp °C. | TBW | BAW | CL | CA | SM | WF |
|---|---|---|---|---|---|---|---|---|---|
| 50 | F, F | Br | oil | — | — | — | — | — | — |
| 51 | F, F | —⌬—OCF₃ | Gum | B | A | A | F | A | G |

TABLE 8

| Compd number | X, Y | R | Mp °C. | TBW | BAW | CL | CA | SM | WF |
|---|---|---|---|---|---|---|---|---|---|
| 52 | F, F | Br | Oil | — | — | — | — | — | — |
| 53 | F, F | ‒⟨C₆H₄⟩‒⟨C₆H₄⟩‒OCF₃ | 81–83 | B | A | A | F | A | G |

TBW refers to activity at 400 ppm against tobacco budworm,

BAW refers to activity at 400 ppm against beet armyworm,

CL refers to activity at 400 ppm against cabbage looper,

CA refers to activity at 50 ppm against cotton aphid,

SM refers to activity at 2.5 ppm against two-spotted spider mite,

WF refers to activity at 200 ppm against whitefly.

In each case the rating scale is as follows:

| % Control | Rating |
|---|---|
| 90–100 | A |
| 80–89 | B |
| 70–79 | C |
| 60–69 | D |
| 50–59 | E |
| less than 50 | F |
| Inactive | G |

Insecticide and Miticide Utility

The compounds of the invention are useful for the control of insects and mites. Therefore, the present invention also is directed to a method for inhibiting an insect or mite which comprises applying to a locus of the insect or mite an insect- or mite-inhibiting amount of a compound of formula (I).

The compounds are useful for reducing populations of insects and mites and are useful in a method of inhibiting an insect or mite population which comprises applying to a locus of the insect or mite an effective insect- or mite-inactivating amount of a compound of formula (I). The "locus" of insects or mites is a term used herein to refer to the environment in which the insects or mites live or where their eggs are present, including the air surrounding them, the food they eat, or objects which they contact. For example, insects or mites which eat or contact edible or ornamental plants can be controlled by applying the active compound to plant parts such as the seed, seedling, or cutting which is planted, the leaves, stems, fruits, grain, or roots, or to the soil in which the roots are growing. It is contemplated that the compounds might also be useful to protect textiles, paper, stored grain, seeds, domesticated animals, buildings or human beings by applying an active compound to or near such objects. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm by weight active compound is used.

For example, insects and mites which can be inhibited include, but are not limited to:

Lepidoptera—Heliothis spp., Helicoverpa spp., Spodoptera spp., *Mythimna unipuncta, Agrotis ipsilon,* Earias spp., *Euxoa auxiliaris, Trichoplusia ni, Anticarsia gemmatalis, Rachiplusia nu, Plutella xylostella,* Chilo spp., *Scirpophaga incertulas, Sesamia inferens, Cnaphalocrocis medinalis, Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae,* Phyllonorycter spp., *Leucoptera malifoliella, Phyllocnisitis citrella*

Coleoptera—Diabrotica spp., *Leptinotarsa decemlineata, Oulema oryzae, Anthonomus grandis, Lissorhoptrus oryzophilus,* Agriotes spp., *Melanotus communis, Popillia japonica,* Cyclocephala spp., Tribolium spp.

Homoptera—Aphis spp., *Myzus persicae,* Rhopalosiphum spp., *Dysaphis plantaginea,* Toxoptera spp., *Macrosiphum euphorbiae, Aulacorthum solani, Sitobion avenae, Metopolophium dirhodum, Schizaphis graminum, Brachycolus noxius,* Nephotettix spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*

Hemiptera—Lygus spp., *Eurygaster maura, Nezara viridula, Piezodorus guildingi, Leptocorisa varicornis*

Thysanoptera—*Frankliniella occidentalis,* Thrips spp., *Scirtothrips dorsalis*

Isoptera—*Reticulitermes flavipes, Coptotermes formosanus*

Orthoptera—*Blattella germanica, Blatta orientalis,* Gryllotalpa spp.

Diptera—Liriomyza spp., *Musca domestica,* Aedes spp., Culex spp., Anopheles spp.

Hymenoptera—*Iridomyrmex humilis,* Solenopsis spp., *Monomorium pharaonis,* Atta spp., Pogonomyrmex spp., Camponotus spp.

Siphonaptera—Ctenophalides spp., *Pulex irritans*

Acarina—Tetranychus spp., Panonychus spp., *Eotetranychus carpini, Phyllocoptruta oleivora, Aculus pelekassi, Brevipalpus phoenicis,* Boophilus spp., *Dermacentor variabilis, Rhipicephalus sanguineus, Amblyomma americanum,* Ixodes spp., *Notoedres cati, Sarcoptes scabiei,* Dermatophagoides spp.

Insecticidal test for tobacco budworm (*Heliothis virescens*), beet armyworm (*Spodoptera exigua*), and cabbage looper (*Trichoplusia ni*).

To prepare test solution, the test compound was formulated at 400 ppm in 7.5 mL of 2 acetone:1 tap water. 250 µL of the test solution was pipetted upon the surface of 8 mL of lepidopteran diet (modified Shorey) contained in each of five one-ounce plastic cups (one cup=1 replication). A $2^{nd}$ instar beet armyworm was placed upon the treated diet in each cup once the solvent had air-dried. The solutions remaining after completing applications to the one-ounce cups were then used as leaf-dip solutions for 3.5 cm leaf discs cut from cabbage leaves and cotton cotyledons. Five discs of each type of plant were dipped until thoroughly coated into each rate of each compound (=5 replications of each treatment). After air-drying, the treated leaf discs were placed individually into one-ounce plastic cups. Each dried, treated cotton cotyledon disc was infested with a $2^{nd}$ instar tobacco budworm larva, and each cabbage leaf disc was infested with a $2^{nd}$ instar cabbage looper larva. Cups containing the treated substrates and larvae were capped and then held in a growth chamber at 25° C., 50–55% RH, and 14 hr light:10 hr dark for 5 days. The number of dead insects of 5 per species per treatment was then determined and the results are given in Table 1–8.

Insecticidal test for cotton aphid (*Aphis gossypii*)

To prepare spray solutions, 1 mg of each test compound was dissolved into 1 mL of a 90:10 acetone:ethanol solvent. This 1 mL of chemical solution was added to 19 mL of water containing 0.05% Tween 20 surfactant to produce a 50 ppm spray solution.

Squash cotyledons were infested with cotton aphid (all life stages) 16–20 hours prior to application of spray solution. The solution was sprayed on both sides of each infested squash cotyledon (0.5 mL×2 each side) with a sweeping action until runoff. The plants were allowed to air dry and held for 3 days in a controlled room at 26° C. and 40% RH after which time the test was graded. Grading was by actual count using a dissecting microscope and comparison of test counts to the untreated check. Results are given in Table 1–8 as percent control based on population reduction versus the untreated.

Insecticidal test for two-spotted spider mite (*Tetranychus urticae*)

Ovicide Method:

Ten adult female two-spotted spider mites were placed on eight 2.2 cm leaf discs of cotton leaf, allowed to oviposit over 24 hours, and thereafter removed. The leaf discs were sprayed with 100 ppm test solutions using a hand syringe, then allowed to dry with sixteen discs left untreated as a negative control. Discs were placed on an agar substrate and held at 24° C. and 90% RH for 6 days. Percent control based on the number of hatched larvae on treated discs and the number on untreated discs is reported in Table 1–8.

Insecticidal test for Sweetpotato Whitefly (*Bemisia tabacia*)

Four mg of each test compound were dissolved by adding 4 mL of a 90:10 acetone:ethanol solvent mixture to the vial containing the sample compound. This solution was added to 16 mL of water containing 0.05% Tween 20 surfactant to produce 20 mL of a 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for two days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (28° C. and 60% RH) for 13 days. Compound efficacy was evaluated by counting, under an illuminated magnifying glass, the number of large nymphs ($3^{rd}$–$4^{th}$ instar) per leaf.

Percent control based on reduction of large nymphs of a test compound compared to solution-only (no test compound) sprayed plants is reported in Table 1–8.

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from -10 ppm to 5000 ppm by weight of compound are expected to provide good control. With many of the compounds, concentrations of from 100 to 1500 ppm will suffice.

The locus to which a compound is applied cam be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect and mite eggs to resist toxicant action, repeated applications may be desirable to control newly emerged larvae, as is true of other known insecticides and acaricides.

We claim:

1. A compound of the formula (I)

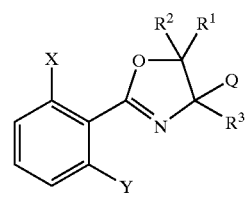

wherein $R^1$ is $(C_1-C_3)$ alkyl or $(C_1-C_3)$ haloalkyl;

$R^2$ and $R^3$ are independently H, halogen, $(C_1-C_3)$ alkyl, $(C_1-C_3)$ haloalkyl, $(C_1-C_3)$ alkoxy or $(C_1-C_3)$ haloalkoxy;

Q is a group selected from

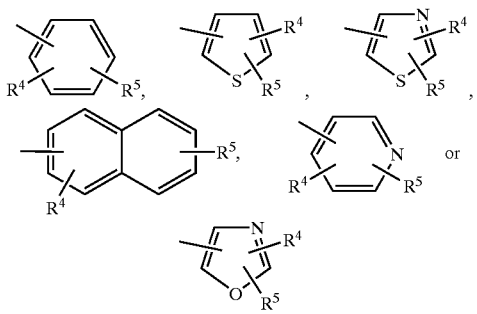

$R^4$ is H, halogen, hydroxy, $(C_1-C_6)$ alkyl, $(C_1-C_6)$ alkoxy, $(C_1-C_6)$ haloalkyl, $(C_1-C_6)$ haloalkoxy, $(C_1-C_6)$ alkoxyalkyl, $(C_1-C_6)$ alkoxyalkoxy, $(C_2-C_6)$ alkenyl, $(C_2-C_6)$ haloalkenyl, CN, $NO_2$, $CO_2R^6$, $CON(R^6)_2$, $S(O)_mR^6$, SCN, $-CH_2OR^6$, $-CH_2SR^6$, $-CH_2NR^6R^6$, $-OCH_2R^6$, $-SCH_2R^6$, $-NR^6CH_2R^6$,

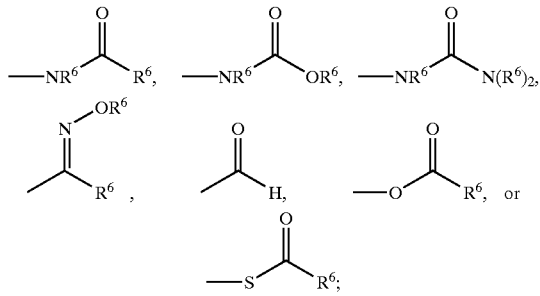

$R^5$ represents

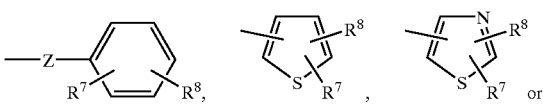

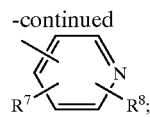

$R^6$ is H, $(C_1-C_6)$ alkyl, $(C_1-C_6)$ haloalkyl, $(C_2-C_6)$ alkenyl, $(C_2-C_6)$ alkynyl, phenyl, or substituted phenyl;

$R^7$ and $R^8$ are independently H, halo, $(C_1-C_6)$ alkyl, $(C_1-C_6)$ haloalkyl, $(C_1-C_6)$ alkoxy or $(C_1-C_6)$ haloalkoxy;

X and Y are independently Cl, F, methyl, halomethyl, methoxy, or halomethoxy;

m is 0, 1, or 2; and

Z is a direct bond, $CH_2$, $CH_2CH_2$, O or S or a phytologically acceptable acid addition salt or N-oxide thereof.

2. A compound of claim 1 in which X and Y are independently F or Cl.

3. A compound of claim 1 in which X and Y are both F.

4. A compound of claim 1 in which $R^2$ and $R^3$ are both H.

5. A compound of claim 1 in which $R^4$ is H, halogen, $(C_1-C_6)$alkyl, $(C_1-C_6)$haloalkyl, $(C_1-C_6)$alkoxy or $(C_1-C_6)$haloalkoxy.

6. A compound of claim 1 in which Q is

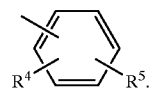

7. A compound of claim 6 in which $R^4$ is H, halogen, $(C_1-C_6)$alkyl, $(C_1-C_6)$haloalkyl, $(C_1-C_6)$alkoxy or $(C_1-C_6)$haloalkoxy.

8. A compound of claim 6 in which $R^5$ is

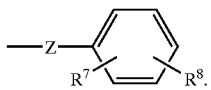

9. A compound of claim 6 in which $R^5$ is

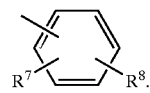

10. A compound of claim 1 in which $R^1$ is methyl.

11. A compound of claim 1 having the formula

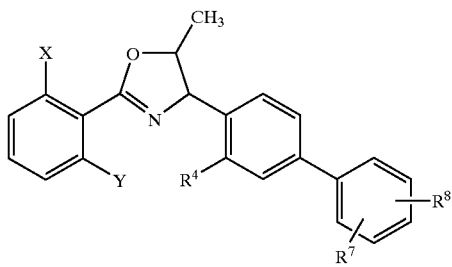

in which X and Y are independently F or Cl and $R^4$, $R^7$ and $R^8$ are independently H, halogen, $(C_1-C_6)$alkyl, $(C_1-C_6)$haloalkyl, $(C_1-C_6)$alkoxy or $(C_1-C_6)$haloalkoxy.

12. A composition for controlling insects or mites which comprises a compound of Formula I

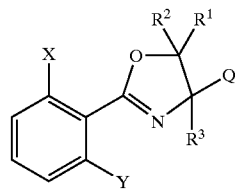

wherein $R^1$ is $(C_1-C_3)$ alkyl or $(C_1-C_3)$ haloalkyl;

$R^2$ and $R^3$ are independently H, halogen, $(C_1-C_3)$ alkyl, $(C_1-C_3)$ haloalkyl, $(C_1-C_3)$ alkoxy or $(C_1-C_3)$ haloalkoxy;

Q is a group selected from

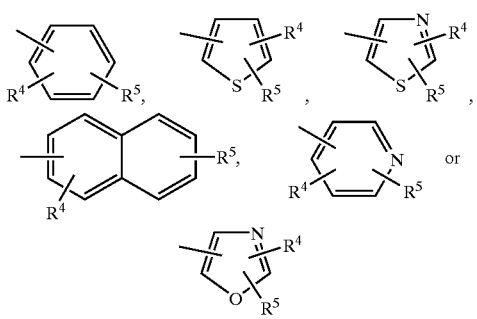

$R^4$ is H, halogen, hydroxy, $(C_1-C_6)$ alkyl, $(C_1-C_6)$ alkoxy, $(C_1-C_6)$ haloalkyl, $(C_1-C_6)$ haloalkoxy, $(C_1-C_6)$ alkoxyalkyl, $(C_1-C_6)$ alkoxyalkoxy, $(C_2-C_6)$ alkenyl, $(C_2-C_6)$ haloalkenyl, CN, $NO_2$, $CO_2R^6$, $CON(R^6)_2$, $S(O)_mR^6$, SCN, $-CH_2OR^6$, $-CH_2SR^6$, $-CH_2NR^6R^6$, $-OCH_2R^6$, $-SCH_2R^6$, $-NR^6CH_2R^6$,

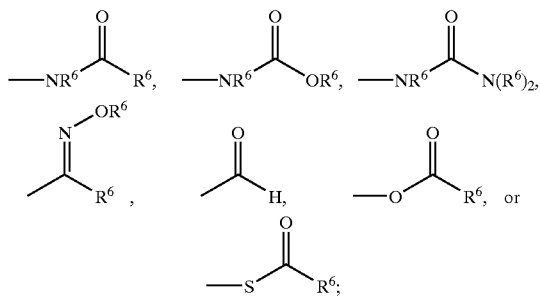

$R^5$ represents

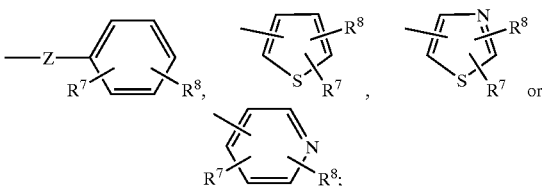

$R^6$ is H, $(C_1-C_6)$ alkyl, $(C_1-C_6)$ haloalkyl, $(C_2-C_6)$ alkenyl, $(C_2-C_6)$ alkynyl, phenyl, or substituted phenyl;

$R^7$ and $R^8$ are independently H, halo, $(C_1-C_6)$ alkyl, $(C_1-C_6)$ haloalkyl, $(C_1-C_6)$ alkoxy or $(C_1-C_6)$ haloalkoxy;

X and Y are independently Cl, F, methyl, halomethyl, methoxy, or halomethoxy;

m is 0, 1, or 2; and

Z is a direct bond, CH$_2$, CH$_2$CH$_2$, O or S or a phytologically acceptable acid addition salt or N-oxide thereof, in combination with a phytologically-acceptable carrier.

13. A composition of claim 12 in which X and Y are independently F or Cl.

14. A composition of claim 12 in which X and Y are both F.

15. A composition of claim 12 in which R$^2$ and R$^3$ are both H.

16. A composition of claim 12 in which R$^4$ is H, halogen, (C$_1$–C$_6$)alkyl, (C$_1$–C$_6$)haloalkyl, (C$_1$–C$_6$)alkoxy or (C$_1$–C$_6$) haloalkoxy.

17. A composition of claim 12 in which Q is

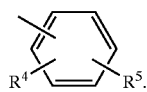

18. A composition of claim 17 in which R$^4$ is H, halogen, (C$_1$–C$_6$)alkyl, (C$_1$–C$_6$)haloalkyl, (C$_1$–C$_6$)alkoxy or (C$_1$–C$_6$) haloalkoxy.

19. A composition of claim 17 in which R$^5$ is

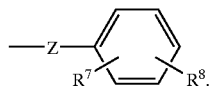

20. A composition of claim 17 in which R$^5$ is

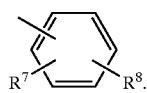

21. A composition of claim 12 in which R$^1$ is methyl.

22. A composition of claim 12 having the formula

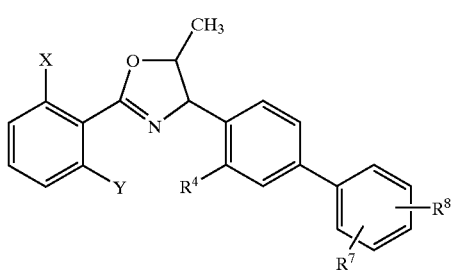

in which X and Y are independently F or Cl and R$^4$, R$^7$ and R$^8$ are independently H, halogen, (C$_1$–C$_6$)alkyl, (C$_1$–C$_6$) haloalkyl, (C$_1$–C$_6$)alkoxy or (C$_1$–C$_6$)haloalkoxy.

23. A method of controlling insects or mites which comprises applying to a locus where control is desired an insect- or mite-inactivating amount of a compound of Formula I

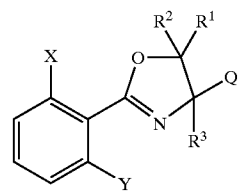

wherein

R$^1$ is (C$_1$–C$_3$) alkyl or (C$_1$–C$_3$) haloalkyl;

R$^2$ and R$^3$ are independently H, halogen, (C$_1$–C$_3$) alkyl, (C$_1$–C$_3$) haloalkyl, (C$_1$–C$_3$) alkoxy or (C$_1$–C$_3$) haloalkoxy;

Q is a group selected from

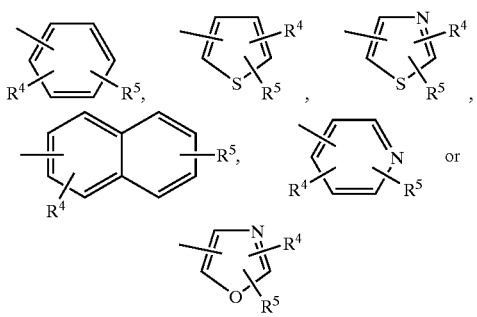

R$^4$ is H, halogen, hydroxy, (C$_1$–C$_6$) alkyl, (C$_1$–C$_6$) alkoxy, (C$_1$–C$_6$) haloalkyl, (C$_1$–C$_6$) haloalkoxy, (C$_1$–C$_6$) alkoxyalkyl, (C$_1$–C$_6$) alkoxyalkoxy, (C$_2$–C$_6$) alkenyl, (C$_2$–C$_6$) haloalkenyl, CN, NO$_2$, CO$_2$R$^6$, CON(R$^6$)$_2$, S(O)$_m$R$^6$, SCN, —CH$_2$OR$^6$, —CH$_2$SR$^6$, —CH$_2$NR$^6$R$^6$, —OCH$_2$R$^6$, —SCH$_2$R$^6$, —NR$^6$CH$_2$R$^6$,

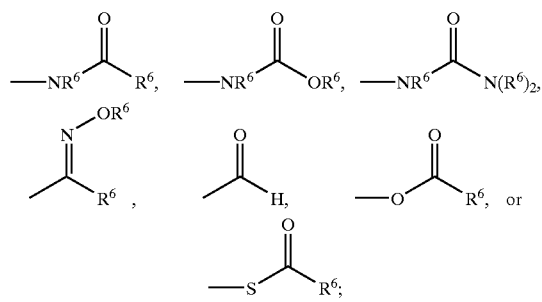

R$^5$ represents

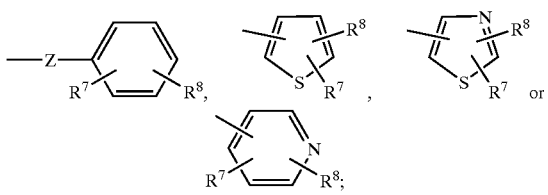

R$^6$ is H, (C$_1$–C$_6$) alkyl, (C$_1$–C$_6$) haloalkyl, (C$_2$–C$_6$) alkenyl, (C$_2$–C$_6$) alkynyl, phenyl, or substituted phenyl;

R$^7$ and R$^8$ are independently H, halo, (C$_1$–C$_6$) alkyl, (C$_1$–C$_6$) haloalkyl, (C$_1$–C$_6$) alkoxy or (C$_1$–C$_6$) haloalkoxy;

X and Y are independently Cl, F, methyl, halomethyl, methoxy, or halomethoxy;

m is 0, 1, or 2; and

Z is a direct bond, $CH_2$, $CH_2CH_2$, O or S or a phytologically acceptable acid addition salt or N-oxide thereof.

24. A method of claim 23 in which X and Y are independently F or Cl.

25. A method of claim 23 in which X and Y are both F.

26. A method of claim 23 in which $R^2$ and $R^3$ are both H.

27. A method of claim 23 in which $R^4$ is H, halogen, $(C_1-C_6)$alkyl, $(C_1-C_6)$haloalkyl, $(C_1-C_6)$alkoxy or $(C_1-C_6)$haloalkoxy.

28. A method of claim 23 in which Q is

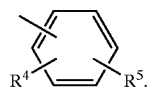

29. A method of claim 28 in which $R^4$ is H, halogen, $(C_1-C_6)$alkyl, $(C_1-C_6)$haloalkyl, $(C_1-C_6)$alkoxy or $(C_1-C_6)$haloalkoxy.

30. A method of claim 28 in which $R^5$ is

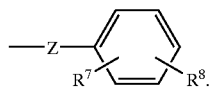

31. A method of claim 28 in which $R^5$ is

32. A method of claim 23 in which $R^1$ is methyl.

33. A method of claim 23 having the formula

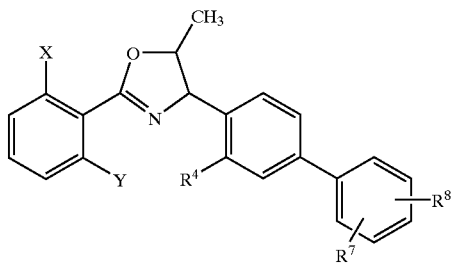

in which X and Y are independently F or Cl and $R^4$, $R^7$ and $R^8$ are independently H, halogen, $(C_1-C_6)$alkyl, $(C_1-C_6)$haloalkyl, $(C_1-C_6)$alkoxy or $(C_1-C_6)$haloalkoxy.

* * * * *